United States Patent
Song et al.

(10) Patent No.: US 6,850,060 B2
(45) Date of Patent: Feb. 1, 2005

(54) METHOD AND APPARATUS FOR RAPID CHARACTERIZATION OF DIFFUSION

(75) Inventors: Yi-Qiao Song, Ridgefield, CT (US); Martin D. Hürlimann, Ridgefield, CT (US); Charles Flaum, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/410,912

(22) Filed: Apr. 10, 2003

(65) Prior Publication Data

US 2003/0197506 A1 Oct. 23, 2003

Related U.S. Application Data

(60) Provisional application No. 60/373,188, filed on Apr. 17, 2002.

(51) Int. Cl.[7] .................................................. G01V 3/00
(52) U.S. Cl. ...................................... 324/303; 324/306
(58) Field of Search ................................. 324/303, 306, 324/300, 307, 309, 312, 314

(56) References Cited

U.S. PATENT DOCUMENTS

| | | | | |
|---|---|---|---|---|
| 5,023,551 A | * | 6/1991 | Kleinberg et al. | 324/303 |
| 5,055,787 A | | 10/1991 | Kleinberg et al. | 324/303 |
| 5,055,788 A | | 10/1991 | Kleinberg et al. | 324/303 |
| 5,153,514 A | | 10/1992 | Griffin et al. | 324/303 |
| 5,796,252 A | | 8/1998 | Kleinberg et al. | 324/303 |
| 6,133,735 A | * | 10/2000 | Hurlimann et al. | 324/303 |
| 6,459,263 B2 | * | 10/2002 | Hawkes et al. | 324/303 |

OTHER PUBLICATIONS

Balibanu, F. et al. "Nuclear Magnetic Resonance in Inhomogeneous Magnetic Fields", *J. Magn. Reson.*, vol. 145, pp. 246–258 (2000).

Bloom, A. L. "Nuclear Induction in Inhomogeneous Fields". *Phys. Rev.*, vol. 98, No. 4, pp. 1105–1116 (1955).

Carr, H. Y. et al. "Effects of Diffusion on Free Precession in Nuclear Magnetic Resonance Experiments", *Phys. Rev.*, vol. 94, No. 3, pp. 630–638 (1954).

de Swiet, T. M. et al. "Decay of nuclear magnetization by bounded diffusion in a constant field gradient", *J. Chem. Phys.*, vol. 100, No. 8, pp. 5597–5604 (1994).

(List continued on next page.)

*Primary Examiner*—Louis Arana
(74) *Attorney, Agent, or Firm*—Jody Lynn DeStefanis; William B. Batzer; John J. Ryberg

(57) ABSTRACT

In one embodiment of the present invention, a method of measuring the molecular displacement of a fluid is disclosed comprising: (a) applying a strong magnetic field gradient to the fluid; (b) applying a sequence of oscillating magnetic field pulses to the fluid wherein the sequence includes a first portion followed by a second portion, wherein the first portion spatially modulates the magnetization state of the fluid and the second portion monitors the evolution of the modulation; (c) detecting magnetic resonance signals from the fluid; and (d) analyzing the detected signals to determine the molecular displacement of the fluid. This method may be used to determine the diffusion of the fluid or the restricted diffusion of the fluid through the porous media if the fluid is within a porous media (such as earth formation, bone, wood or other material). Also disclosed is a logging tool configured to implement this methodology.

35 Claims, 10 Drawing Sheets

OTHER PUBLICATIONS

Goelman, G. et al. "The CPMG Pulse Sequences in Strong Magnetic Field Gradients with Applications to Oil–Well Logging", *J. Magn. Reson.*, Series A, vol. 113, pp. 11–18 (1995).

Hahn, E. L. "Spin Echoes", *Phys. Rev.*, vol. 80, No. 4, pp. 580–594 (1950).

Hennig, J. "Multiecho Imaging Sequences with Low Refocusing Flip Angles". *J. Magn. Reson.* vol. 78, pp. 397–407 (1988).

Hurlimann, M. D. et al. "Dephasing of Hahn Echo in Rocks by Diffusion in Susceptibility–Induced Field Inhomogeneities". *Magn. Reson. Imaging*, vol. 16, pp. 535–539 (1998).

Hurlimann, M. D. "Optimization of timing in the Carr Purcell–Meiboom–Gill sequence", *Magn. Reson. Imaging*, vol. 19, pp. 375–378 (2001).

Hurlimann, M. D. "Diffusion and Relaxation Effects in General Stray Field NMR Experiments". *J. Magn. Reson.* vol. 148, pp. 367–378 (2001).

Hurlimann, M. D. et al. "Quantitative Measurement of Two–Dimensional Distribution Functions of Diffusion and Relaxation in Grossly Inhomogeneous Fields". *J. Magn. Reson.* vol. 157, pp. 31 (2002).

Hurlimann, M. D. et al. "The diffusion–spin relaxation time distribution function as an experimental probe to characterize fluid mixtures in porous media". *Journal of Chemical Physics*, vol. 117, No. 22, pp. 10223–10232 (2002).

Kaiser, R. et al. "Diffusion and field–gradient effects in NMR Fourier spectroscopy", *J. Chem. Phys.*, vol. 60, No. 8, pp. 2966–2979 (1974).

Kleinberg, R. L. et al. "NMR Properties of Reservoir Fluids". *The Log Analyst*, pp. 20–32 (Nov.–Dec. 1996).

Latour, L. L. et al. "Pore–Size Distributions and Tortuosity in Heterogeneous Porous Media".*J. Magn. Reson.*, Series A, 112, pp. 83–91 (1995).

Meiboom, S. et al. "Modified Spin–Echo Method for Measuring Nuclear Relaxation Times". *The Review of Scientific Instruments*, vol. 29, No. 8, pp. 688–691 (Aug. 1958).

Mitra, P. P. et al. "Diffusion Propagator as a Probe of the Structure of Porous Media". *Phys. Rev. Lett.*, vol. 68, No. 24, pp. 3555–3558 (1992).

Oshio, K. et al. "Fast MRI by Creating Multiple Spin Echoes in a CPMG Sequence". *Magn. Reson. Med.*, vol. 30, pp. 251–254 (1993).

Packer, K. J. "The study of slow coherent molecular motion by pulsed nuclear magnetic resonance". *Molecular Physics*, vol. 17, No. 4, pp. 355–368 (Oct. 1969).

Ross, A. et al. "Systematic Errors Associated with CPMG Pulse Sequence and their Effect on Motional Analysis of Biomolecules". *J. Magn. Reson.* vol. 124, pp. 355 (1997).

Sen, P. N. et al. "Surface relaxation and the long–time diffusion coefficient in porous media: Periodic geometries". *Physical Review B*, vol. 49, No. 1, pp. 215–230 (1994).

Sen, P. N. et al. "Spin echoes of nuclear magnetization diffusing in a constant magnetic field gradient and in a restricted geometry". *J. Chem. Phys.*, vol. 111, pp. 6548 (1999).

Simbrunner, J. et al. "Analysis of Carr–Purcell Sequences with Nonideal Pulses".*J. Magn. Reson.*, vol. B, 109, pp. 301 (1995).

Sodickson A. et al. "A generalized k–space formalism for treating the spatial aspects of a variety of NMR experiments". *Prog. NMR Spectrosc.*, vol. 33, pp. 77–108 (1998).

Solomon, I. "Relaxation Processes in a System of Two Spins". *Physical Review*, vol. 99, No. 2, pp. 559–565 (Jul. 1955).

Song, Y.–Q. Categories of Coherence Pathways in the CPMG Sequence. *J. Magn. Reson.* vol. 157, pp. 82–91 (2002).

Stejskal, E. O et al. "Spin Diffusion Measurements: Spin Echoes in the Presence of a Time–Dependent Field Gradient". *J. Chem. Phys.*, vol. 42, No. 1, pp. 288–292 (Jan. 1965).

Tanner, J. E. et al. "Restricted Self–Diffusion of Protons in Colloidal Systems by the Pulsed–Gradient, Spin–Echo Method", *J. Chem. Phys.*, vol. 49, No. 4, pp. 1768–1777 (Aug. 1968).

Wayne, R. C. et al. "Nuclear–Magnetic–Resonance Study of Self–Diffusion in a Bounded Medium", *Phys. Rev.*, vol. 151, No. 1, pp. 264–272 (Nov. 1966).

Woessner, D. E. "Effects of Diffusion in Nuclear Magnetic Resonance Spin–Echo Experiments". *J. Chem. Phys.*, vol. 34, pp. 2057–2061 (1961).

Woessner, D. E. "N.M.R. Spin–Echo Self–Diffusion Measurements on Fluids Undergoing Restricted Diffusion". *J. Phys. Chem.*, vol. 67, pp. 1365–1367 (Jun. 1963).

Zielinski, L. J. et al. "Relaxation of nuclear magnetization in a nonuniform magnetic field gradient and in a restricted geometry". *J. Magn. Reson.*, vol. 147, pp. 95 (2000).

Callaghan, Paul T. "Principles of Nuclear Magnetic Resonance Microscopy". Clarendon Press (1991), pp. 93–96.

* cited by examiner

METHOD AND APPARATUS FOR RAPID CHARACTERIZATION OF DIFFUSION

This patent application claims priority from U.S. Provisional Application No. 60/373,188 filed on Apr. 17, 2002, which is incorporated herein by reference in its entirety.

FIELD OF THE INVENTION

The present invention relates to the use of Nuclear Magnetic Resonance (NMR) to determine the molecular displacement of a fluid and, more particularly, to the use of CPMG and KCPMG to determine diffusion of a fluid or restricted diffusion of a fluid in a porous media.

BACKGROUND

Measurement of the diffusion constant can assist the characterization of molecules and fluids. The time dependent diffusion constant can be used to characterize pore geometry, such as surface-to-volume ratio and tortuosity and it has been used to study rocks by applying pulsed or static field gradients. In these NMR measurement (using spin echo and stimulated echo for example), one diffusion time ($\Delta$) will be preset in the pulse sequence to determine the molecular displacement over $\Delta$, thus obtaining D($\Delta$). Then, a series of measurements are made with different $\Delta$'s to acquire the full curve of the time-dependent diffusion constant. Measurements of diffusion using CPMG (Carr-Purcell-Meiboom-Gill) sequence alone would result in $\Delta$ comparable to the time between the $\pi/2$ and the first $\pi$ pulses.

K. J. Packer, as described in "The study of slow coherent molecular motion by pulsed nuclear magnetic resonance," Mol. Phys. 17, 355 (1969) (incorporated by reference herein in its entirety), used NMR to monitor flow rate in the presence of a weak magnetic field gradient. Packer does not recognize that a more robust measurement may be made using a strong magnetic field gradient or that diffusion and restricted diffusion measurements may be made in the presence of a strong field gradient.

Further, the conventional methods do not account for contributions from many different pathways.

Accordingly, it is an object of the present invention to provide a method that provides information regarding molecular displacement, and in particular, diffusion and restricted diffusion of a fluid (gas or liquid) in bulk or in a porous media.

SUMMARY OF THE INVENTION

The present invention provides a method to monitor the molecular displacement of a fluid. The fluid may be unbound (i.e., bulk) or bound (i.e., in a porous media). While this method may be used for any porous media (such as bone, wood, food, etc.), it is particularly useful to measure diffusion and restricted diffusion of oil or other hydrocarbons in bulk or in an earth formation.

More specifically, the present invention discloses a method to determine the molecular displacement at many values of $\Delta$ in one or a few scans of a modified CPMG sequence, called KCPMG. In the present invention, a CPMG sequence is modified to include a spatially modulated magnetization at the beginning portion of the sequence and then uses the CPMG $\pi$ pulse train to monitor the evolution of the modulation. In contrast, the initial magnetization in CPMG is uniform. In the case of spatial diffusion, the amplitude of the magnetization modulation is governed by the diffusion dynamics. Accordingly, the present invention measures directly the time dependent diffusion.

The KCPMG concept used herein is closely related to the early work of K. J. Packer as described in "The study of slow coherent molecular motion by pulsed nuclear magnetic resonance," Mol. Phys. 17, 355 (1969) wherein the flow of fluids was monitored, using a rather weak field gradient. However, in the present invention a strong magnetic field gradient is used to change the behavior of the echo formation to include contributions from many coherence pathways. In fact, such large field inhomogeneities lead to a consistent echo shape that facilitates the determination of diffusion properties.

In one embodiment of the present invention, a method of measuring the molecular displacement of a fluid is disclosed comprising: (a) applying a strong magnetic field gradient to the fluid; (b) applying a sequence of oscillating magnetic field pulses to the fluid wherein the sequence includes a first portion followed by a second portion, wherein the first portion spatially modulates the magnetization state of the fluid and the second portion monitors the evolution of the modulation; (c) detecting magnetic resonance signals from the fluid; and (d) analyzing the detected signals to determine the molecular displacement of the fluid. The methodology may be employed wherein (b) and (c) are repeated one or more times. This method may be used to determine the diffusion of the fluid or the restricted diffusion of the fluid through a porous media (such as earth formation, bone, wood or other material). Further, the velocity and acceleration of the fluid may also be determined.

For the purposes of the present invention, a magnetic field gradient is considered to be strong if it is greater than $1/\gamma L t_\pi$. Further, the strong magnetic field gradient may be grossly inhomogeneous.

Any sequence may be used that includes a first portion that spatially modulates the magnetization state (such as KCPMG) and a second portion that monitors the evolution of the spatial modulation (such as a CPMG-like sequence). Accordingly, a modified CPMG sequences may be used in accordance with the present invention wherein the first portion of the sequence includes an extra time delay:

$$\frac{\pi}{2} - T_m - T'_{cp} - [\pi - 2T_{cp}]_N.$$

Alternatively, $$\frac{\pi}{2} - \delta - \frac{\pi}{2} - T_d - \frac{\pi}{2} - T_{cp} - [\pi - 2T_{cp}]_n$$

or $$\frac{\pi}{2} - \frac{\delta}{2} - \theta_1 - \frac{\delta}{2} - \theta_2 - T_{cp} - [\pi - 2T_{cp}]_n$$

sequences may be used. Preferably, the sequence chosen should produce more than one (1) echo.

A second embodiment of the present invention is an apparatus to employ the methodology in a borehole, comprising a logging tool that is moveable through a formation containing a fluid; and a processor that is coupled with the logging tool, the processor being programmed with instructions which, when executed by the processor cause the logging tool to: i) generate a sequence of oscillating magnetic field pulses to said fluid wherein said sequence includes a first portion followed by a second portion, wherein said first portion spatially modulates the magnetization state of the fluid and said second portion monitors the evolution of said modulation, wherein said sequence is generated in the presence of a strong magnetic field gradient; ii) detect magnetic resonance signals produced from said fluid; and cause the processor to analyze the detected magnetic resonance signals to determine any molecular displacement of said fluid.

In a third embodiment, a method of measuring magnetization transfer by chemical exchange of a sample is disclosed comprising: applying a sequence of oscillating magnetic field pulses to the sample wherein the sequence includes a first portion followed by a second portion, wherein said first portion induces a chemical shift modulation of the sample and the second portion monitors the evolution of the modulation; detecting magnetic resonance signals from the sample; and analyzing the detected signals to determine the magnetization transfer of the sample.

Further features and applications of the present invention will become more readily apparent from the figures and detailed description that follows.

DETAILED DESCRIPTION

KCPMG Methodology
CPMG and Coherence Pathways

The conventional CPMG sequence begins with a π/2 radio-frequency (RF) pulse, a waiting period $T_{cp}$, followed by a train of π pulses separated in time by $2T_{cp}$. This is commonly described by:

$$\frac{\pi}{2} - T_{cp} - [\pi - 2T_{cp}]_N \tag{1}$$

The brackets denote the repeating unit and N is the total number of echoes. The acquisition of echoes is made between the adjacent pairs of π pulses. In the present invention a constant field gradient (G) is applied during the CPMG and all other pulse sequences. In a strong field gradient, the delay after the initial π/2 pulse (of length $t_{\pi/2}$) should be reduced to $$T'_{cp} = T_{cp} - \frac{2t_{\frac{\pi}{2}}}{\pi}$$

in order to compensate for the precession during the π/2 pulse (see M. D. Hurlimann, "Optimization of timing in Carr-Purcell-Meiboom-Gill sequence," Magn. Reson. Imaging 19, 375 (2001), incorporated by reference herein in its entirety):

$$\frac{\pi}{2} - T'_{cp} - [\pi - 2T_{cp}]_N \tag{2}$$

It is beneficial to discuss the CPMG-related sequences in terms of coherence pathways, in particular, for experiments in strong field gradients when the signal bandwidth is limited by the power of RF pulses (see R. Kaiser et al., "Diffusion and field gradient effects in NMR Fourier spectroscopy," J. Chem. Phys. 60, 2966 (1974), incorporated by reference herein in its entirety). In these strong field gradients, the nutation angle and the orientation of the rotation axis of a pulse depend on the offset between the frequency of the spin's Larmor precession and the RF irradiation (see A. L. Bloom, "Nuclear induction in inhomogeneous fields," Phys. Rev. 98, 1105 (1995) and J. Hennig, "Multiecho imaging sequences with low frequency flip angles," J. Magn. Reson. 78, 397 (1988), incorporated by reference herein in their entireties). As a result, many trajectories of the magnetization evolution contribute to the echo signals as disclosed in the following articles, all of which are incorporated by reference herein in their entireties:

1. G. Goelman et al., "The CPMG pulse sequence in strong magnetic field gradients with applications to well logging," J. Magn. Reson. A 113, 11 (1995)
2. J. Simbrunner et al., "Analysis of Carr-Purcell sequences with nonideal pulses," J. Magn. Reson. B 109, 301 (1995)
3. A. Ross et al., "Systematic errors associated with CPMG pulse sequence and their effect on motional analysis of biomolecules," J. Magn. Reson. 124, 355 (1997)
4. F. Bãlibanu et al., "Nuclear magnetic resonance in inhomogeneous magnetic field," J. Magn. Reson. 145, 246 (2000) and
5. M. D. Hurlimann, "Diffusion and relaxation effects in general stray field NMR experiments," J. Magn. Reson. 148, 367 (2001).

Figure 1A:
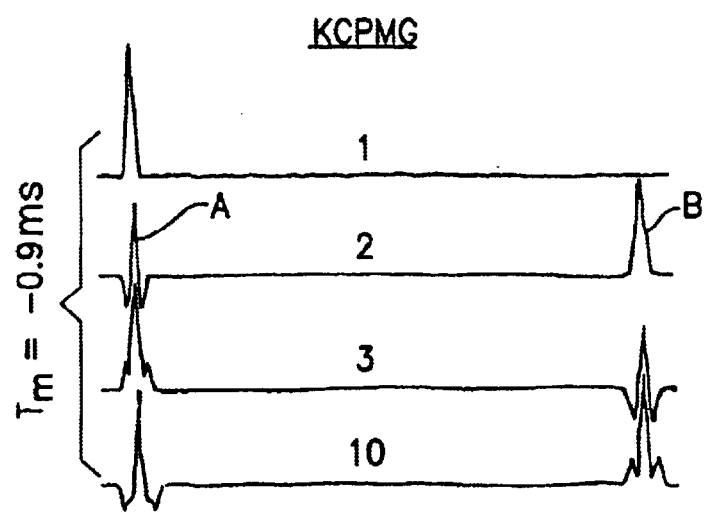
FIGS. 1(a)–(d) are graphical depictions of CPMG and KCPMG echoes versus the detection time starting after the π pulse in accordance with the present invention.

For the purposes of this discussion, the magnetization states are described using the following notation: q can be 0, +1, or −1, (or 0, + and −), corresponding to z-, clockwise, or counterclockwise precessing magnetizations, respectively. The RF pulses rotate the magnetization vector and thus change q. A coherence pathway is characterized by a series of numbers, $Q_N \equiv (q_0, q_1, \ldots, q_N)$, where $q_0$ is the coherence before the first π pulse and N is the echo number. Two types of coherences, the direct spin echo (SE) and the stimulated echo (STE) may be used. The direct spin echo is characterized by a series of "q"s that alternate between + and −. The stimulated echoes, on the other hand, have a few "q"s being zero corresponding to magnetization along the z-axis. For the CPMG sequence, the echoes for these two types of pathways form midway between two adjacent π pulses as shown in FIG. 1(c). However, in KCPMG, the echoes form at different times as shown in FIGS. 1(a), (b) and (d).

The contribution of a coherence pathway to the $N^{th}$ echo can be written as a product of two factors, $M_{Q_N} = A_Q \cdot S_Q$. $A_Q$ is a factor determined by the RF pulses. For a given coherence pathway, it can be identical for KCPMG and CPMG. $S_Q$ describes the decay factor due to diffusion for a coherence pathway and is independent of the frequency offset. $S_Q$ for KCPMG is different from that for CPMG. As a result, KCPMG is sensitive to diffusion over long diffusion times.

KCPMG Pulse Sequence

The concept of KCPMG can be implemented in several different ways. The simplest form is comprised of a CPMG sequence with an extra delay $T_m$ inserted between the first π/2 and π pulses:

$$\frac{\pi}{2} - T_m - T'_{cp} - [\pi - 2T_{cp}]_n \quad (3)$$

$T_m$ can be positive or negative and $|T_m| = \delta < T_{cp}$. For positive $T_m$, the duration between the π/2 and the first π pulse is $T_{cp} + \delta$, and for negative $T_m$, it is $T'_{cp} - \delta$. CPMG sequence corresponds to $T_m = 0$. It is assumed here that a constant magnetic field gradient G is applied. The same RF sequence was considered by K. J. Packer with a weak gradient, i.e. $\gamma G L t_\pi < 1$, where $\gamma$ is the gyromagnetic ratio of the detected nuclei, G is the magnetic field gradient, and L is the sample length along the gradient direction. In this case, the RF pulses can excite the entire sample and the nutation angle of the π pulse is close to 180 degrees for the entire sample. Thus, the magnetization is well refocused by the π pulses for the early echoes and these echo signals are dominated by one main coherence pathway (direct echo). This can also be accomplished by including gradient pulses between the RF pulses, for example. However, for the later echoes, effects from minute errors of the pulses and RF field inhomogeneity will become significant so that other coherence pathways may not be neglected. As a result, the echo amplitude and shape will change and likely oscillate. In the present invention, a strong field gradient, $\gamma G L t_\pi > 1$ is used. This changes the spin dynamics by allowing many more coherence pathways to contribute appreciably. As described below, this condition produces consistent echo shapes, which is helpful for an interpretation of the echo signal.

Phase cycling was used to select only coherence pathways that produce transverse magnetization after the first π/2 pulse. For the pulse sequences in Eq. 1 and 3, the phase of the first π/2 pulse was alternated between 0 and 180 degrees. The π pulses were at 90 degree phase. The data from the two phase settings are subtracted from each other.

A similar RF sequence coupled with pulsed field gradients has also been reported by K. Oisho et al. in "Fast MRI by creating multiple spin echoes in a CPMG sequence," Magn. Reson. 30, 251 (1993) (incorporated by reference herein in its entirety) with a goal of producing multiple echoes and accelerating imaging experiments.

Echo Shapes

The peaks of KCPMG echoes form at times shifted by +δ (late echoes) or −δ (early echoes) relative to the corresponding positions of the CPMG echoes ($\delta = |T_m|$). The shapes of several echoes obtained with the CPMG (Eq. 2) and KCPMG (Eq. 3) sequences are compared in FIGS. 1(a)–(d), which show CPMG and KCPMG echoes versus the detection time starting after the π pulse, for tap water at $\delta = 0.9$ ms and $T_{cp} = 1.1$ ms. The data for each signal is labeled by the echo number. The sample shape is a cylinder of 2 cm diameter and 4 cm length. The magnetic field is 410 G corresponding to the proton Larmor frequency of 1.7 MHz. The applied magnetic field gradient is 13.2 G/cm and the duration of the π/2 pulse is 12 μs. Only a slice of about 5 mm in the center of the sample was excited by the RF pulses. Experiments were performed using an Apollo spectrometer from Tecmag.

FIGS. 1(a) and (b) show the KCPMG echoes with $T_m = -0.9$ and $+0.9$ ms, and $\delta = 0.9$ ms. FIG. 1(c) shows the shape of the CPMG echoes from the first Hahn echo to the later ones with the asymptotic echo shape in a constant field gradient. It is typical for the CPMG asymptotic echo to develop small negative amplitudes at the edges of the echo. The first echo occurs at a time $T_{cp} - \delta$ after the π pulse and has the shape of the Hahn echo because the direct echo is the only possible coherence pathway. The second detection period displayed below shows two echoes appearing at times $T_{cp} + \delta$ and $T_{cp} - \delta$ after the second π pulse. The two echoes, shown as A and B in FIGS. 1(a), (b) and (d), have different shapes because they are formed by different coherence pathways, with the early one, A, being a stimulated echo (Q=+0−) and the late one, B, being a direct echo (Q=−+−). For echoes in the later periods after many π pulses, both direct and stimulated echolike coherence pathways contribute giving rise to their unique, asymptotic shapes. The echoes at times $T_{cp} + T_m$ are contributed by the coherence pathways starting with $q_0 = -1$, while the echoes at times $T_{cp} - T_m$ are contributed by those starting with $q_0 = +1$. For CPMG, i.e., $T_m = 0$, the signals from these different coherence pathways overlap midway between two π pulses. The non-zero $T_m$ in KCPMG allows the separate observation of these different coherence pathways directly. For the second echo, this technique has also been used by Bálibanu et al. to separate the two contributions.

Figure 1B:
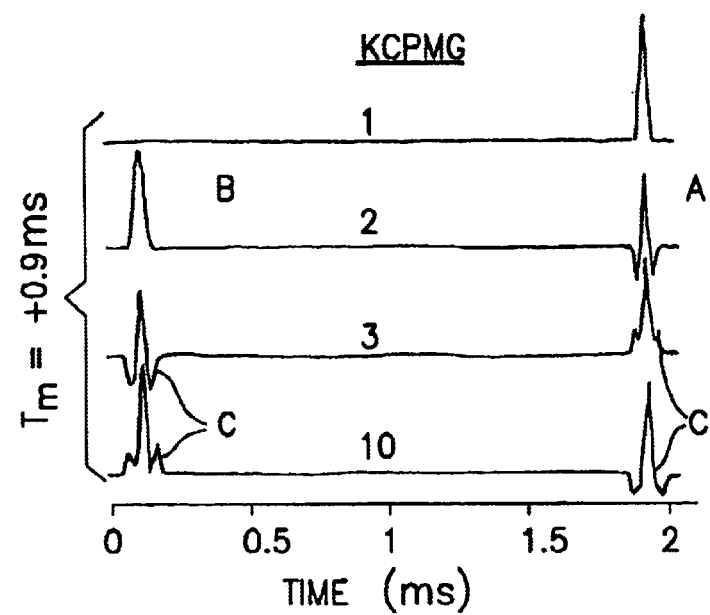
Figure 1C:
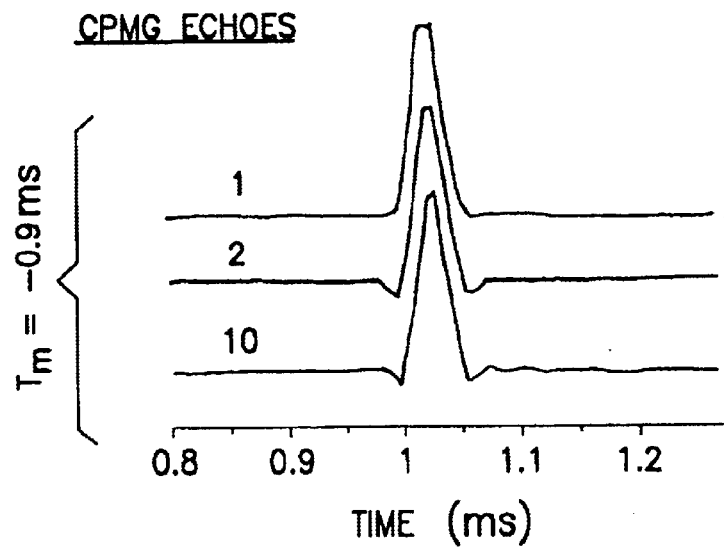
Figure 1D:
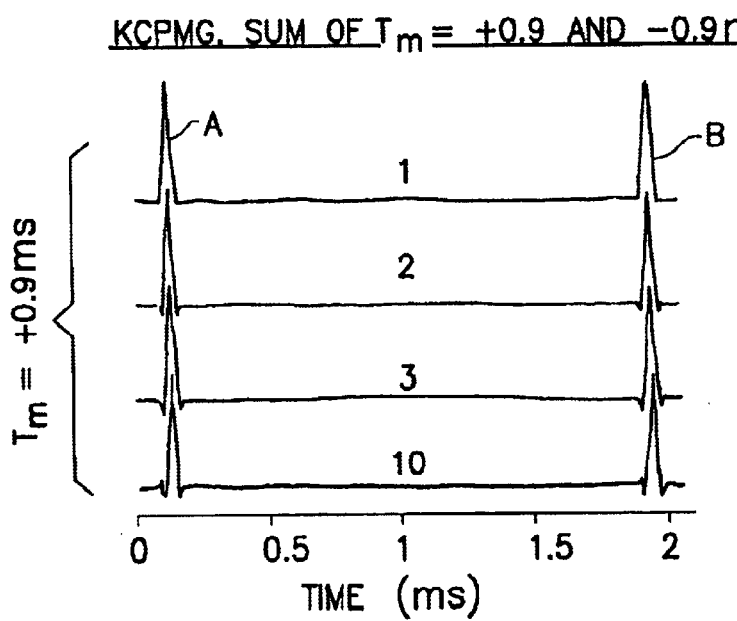

The KCPMG sequence (Eq. 3) with positive $T_m$ produces a similar echo evolution as discussed above for negative $T_m$, but with the early A and late B echoes reversed, FIG. 1(b). The addition of the data from sequences with $T_m$ and $-T_m$ (FIG. 1(d)) cancels much of the secondary features as shown by C in FIGS. 1(b) and (d) of the echoes and makes the shapes of the KCPMG echo much more similar to those of the CPMG echoes. In this symmetrized form, the same coherence pathways contribute to both the early and late KCPMG echoes and these pathways are identical to those of the corresponding CPMG echoes. Thus, this is the preferred scheme to execute the KCPMG.

Decay Due to Diffusion

The decay of signal from the fluids during the CPMG in the presence of field gradients is dominated by two sources. The first source is the intrinsic bulk spin-spin relaxation and relaxation due to interactions with the surfaces. The second source is the Brownian motion of fluid molecules in the presence of inhomogeneous magnetic fields. At the middle of the adjacent π pulses, the accumulated phase from Larmor precession is zero on average; however, the phase dispersion due to diffusion renders some of the spins out of phase leading to signal decay. Because the average phase is zero, the final effect of diffusion is an attenuation of the signal.

Although the KCPMG sequence (Eq. 3) may appear almost identical to CPMG, the spin dynamics retains an additional element of evolution. It is instructive to view the KCPMG pulse sequence in two segments or portions. The first segment includes the first π/2 pulse and the following time period $T_m$ and spatially modulates the magnetization state (as discussed below). The second segment starts at the end of $T_m$ and extends to the rest of the sequence and monitors the evolution of the modulation (as discussed below). This second segment is identical to the CPMG sequence because the magnetization starts in the transverse plane. For the CPMG sequences, at any time in the middle of the two adjacent π pulses, the average phase is zero and the effect of diffusion may be quantified as an attenuation factor. This attenuation factor can be obtained from a CPMG measurement with the same $T_{cp}$.

The presence of the first segment produces a spatially modulated magnetization at time $T_m$ with a modulation wavelength:

$$\lambda = 2\pi/(\gamma G \delta) \tag{4}$$

where γ is the gyromagnetic ratio of the detected nuclei and G is the magnetic field gradient. A wave vector may also be defined as $$K \equiv 2\pi/\lambda = \gamma G \delta \tag{5}$$

as in magnetic resonance imaging (see A. Sodickson et al., "A generalized k-space formalism for treating the spatial aspects of a variety of NMR experiments," Prog. NMR Spectroscop. 33, 77 (1998), incorporated by reference herein in its entirety). These K-states of magnetization modulation, hence the name "KCPMG", are the eigenstates of diffusion in bulk fluids and the amplitude of the K-states decays exponentially (see P. N. Sen et al., "Surface relaxation and the long-time diffusion coefficient in porous media: Periodic geometries," Phys. Rev. B 49, 215 (1994), incorporated by reference herein in its entirety) with the decay rate:

$$R(K) = DK^2 \tag{6}$$

where D is the diffusion constant, defined from the mean square displacement ($<r^2>$), $D=<r^2>/6\Delta$, where $\Delta$ is the observation time. In bulk fluids, D is a constant. For diffusion in porous media, the above sinusoidal modulation is no longer the eigenstate of the diffusion dynamics resulting in that D can depend on $\Delta$.

Thus, the effect of the first part of KCPMG is to prepare a spatially modulated magnetization state and the second part monitors the evolution of this K-state. The KCPMG echoes appearing off center should be viewed as the time-domain signal of the K-states with the time origin at the CPMG echo position. On the other hand for the case of the CPMG, the initial state is a spatially uniform magnetization. Thus, it would be expected that the signals from KCPMG sequence will have an additional decay $\exp[-R(K)t]$:

$$S(K,t) \approx S(0,t) \cdot e^{-DK^2 t} \tag{7}$$

where t is echo time, $t=2NT_{cp}$ and N is the echo number. The signal $S(0, t)$ is in fact the CPMG data because it corresponds to $T_m=0$ and thus K=0. Detailed spin dynamics calculations including the effects of finite pulse length and gross field inhomogeneity have confirmed that Eq. 7 is a good ansatz.

Correction for Spin-Spin Relaxation

For samples with short relaxation times, a correction term should be added to Eq. 7. Because the KCPMG echoes appear at different times than the CPMG echoes, transverse relaxation affects KCPMG and CPMG differently if relaxation is important during the time δ. For example, with $T_m=+\delta$, the two $N^{th}$ echoes of the KCPMG sequence appear at $2NT_{cp}$ and $2NT_{cp}+2\delta$ after the initial π/2 pulse. Thus, a correction term to compensate for such different echo times can be included in Eq. 7:

$$S(K,t) \approx S(0,t) \cdot \frac{1}{4}(2 + e^{-2\delta/T_2} + e^{2\delta/T_2}) \cdot e^{-DK^2 t} \tag{8}$$

where $T_2$ is the spin-spin relaxation of the fluid, including surface contributions. "A" shall denote the relaxation factor:

$$A \equiv \frac{1}{4}(2 + e^{-2\delta/T_2} + e^{2\delta/T_2}).$$

For $\delta << T_2$ as is the case for the experiments discussed below, A can be well approximated by 1.

Alternative KCPMG Sequences

There are various means to create the initial spatial modulation of the magnetization essential for the KCPMG concept. In a second implementation a z-magnetization modulation is created and refocused with the following sequence:

$$\pi/2 - \delta - \pi/2 - T_d - \pi/2 - T_{cp} - [\pi - 2T_{cp}]_n \tag{9}$$

The phases used for the first three pulses are: (0 180), (0 0 180 180), and 0 degree. The phase of all π pulses is 90 degree. The receiver phases are: 0 180 180 0. The first π/2 pulse rotates the magnetization to the transverse plane for precession under the field gradient. The second π/2 pulse stores the magnetization modulation along the longitudinal direction. The wavelength of the modulation is again given by Eq. 4. The transverse magnetization at the end of the second π/2 pulse can be removed by proper phase cycling or inclusion of a crusher gradient. The rest of the sequence is identical to the CPMG. The first three pulses form the usual stimulated echo sequence and $T_d$ is the initial diffusion time. The first echo after the third π/2 pulse is a stimulated echo. For the $N^{th}$ echo, the diffusion time is $\Delta = T_d + 2NT_{cp}$.

More complex modulation scheme can be implemented in the initial part of the sequence. For example, if an initial modulation is comprised of a superposition of uniform magnetization with a modulated magnetization, then one scan of the KCPMG sequence can obtain decays for multiple values of K.

In an example of such complex modulation, the CPMG sequence is preceded by three pulses:

$$\pi/2 - \delta/2 - \theta_1 - \delta/2 - \theta_2 - T_{cp} - [\pi - 2T_{cp}]_n \tag{10}$$

where $\theta_1$ and $\theta_2$ are RF pulses with tipping angles $\theta_1$ and $\theta_2$. The first two pulses create magnetization with a modulation characterized by $K = \pm K_0, \pm K_0/2$ and 0, where $K_0 = \gamma G \delta$. The tipping angle $\theta_2$ of the third pulse as well as the phase cycling for the first three pulses control the weight of the different modulations. Five echoes will be observed between the adjacent π pulses. Echoes for different modulations are shifted by a different time, $\pm |K|/(\gamma G)$, from the nominal CPMG echo position. Thus, in a single scan three decays for $|K|=0, K_0/2, K_0$ can be obtained simultaneously.

Experimental Verifications

Bulk Fluids

The KCPMG technique was tested on a sample of tap water using a Bruker AVANCE™ NMR spectrometer (manufactured by Bruker BioSpin GmbH) at a proton Larmor frequency of 85 MHz. The pulse sequence in Eq. 9 was used with an additional crusher gradient during $T_d$ to remove the transverse components. A z-gradient of 10 G/cm was applied during the encoding and CPMG. A y-gradient of 5 G/cm was used during the crusher period ($T_d$). $T_{cp}$ was 2 ms and $T_m$ varied from 0.5 to 1.9 ms.

Figure 2:
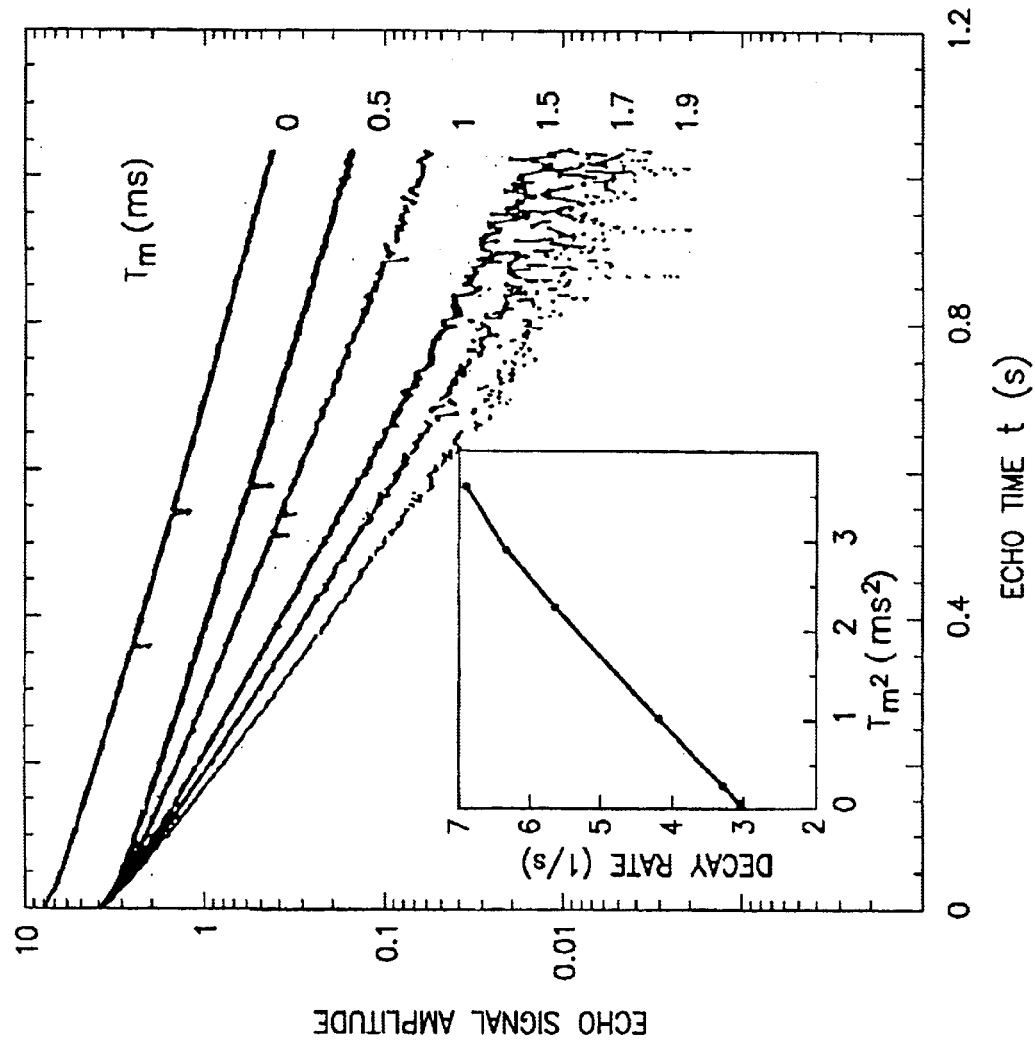
FIG. 2 is a graphical depiction of KCPMG measurements for water at several $T_m$'s; the inset shows the decay rate R for KCPMG as a function of $T_m^2$.

FIG. 2 shows KCPMG measurements for water at several $T_m$'s. The CPMG data corresponds to $T_m=0$. The pulse sequence used was Eq. 9, $T_{cp}=2$ ms and $T_d=5.3$ ms. The magnetic field gradient applied during the encoding and CPMG is 10 G/cm along z. A crusher gradient of 5 G/cm (y) was applied during $T_d$. Signals were acquired at the peak of the early echoes. In the inset, decay rate R for KCPMG is shown as a function of $T^2_m$. The linear dependence of R with $T^2_m$ is consistent with Eq. 6 and the extracted diffusion constant for water is $1.5\times10^{-5}$ cm$^2$/s at 14 degrees C. The apparent glitches in the data were caused by intermittent receiver problems. As shown in FIG. 2, the decay for all values of $T_m$ is approximately exponential and the decay rate increases as $T_m$ increases. The initial KCPMG signals are about half of the CPMG signal because only one KCPMG echo was detected. The signals of early echoes showed additional oscillations due to the evolution in the echo shape. The decay rate for each value of $T_m$ was calculated from the data and plotted in the inset of FIG. 2 as a function of $T_m^2$. The linearity and values of the additional decay rate is consistent with Eq. 6 for the decay of K-modes. Therefore, these data are consistent with Eq. 7.

Figure 3:
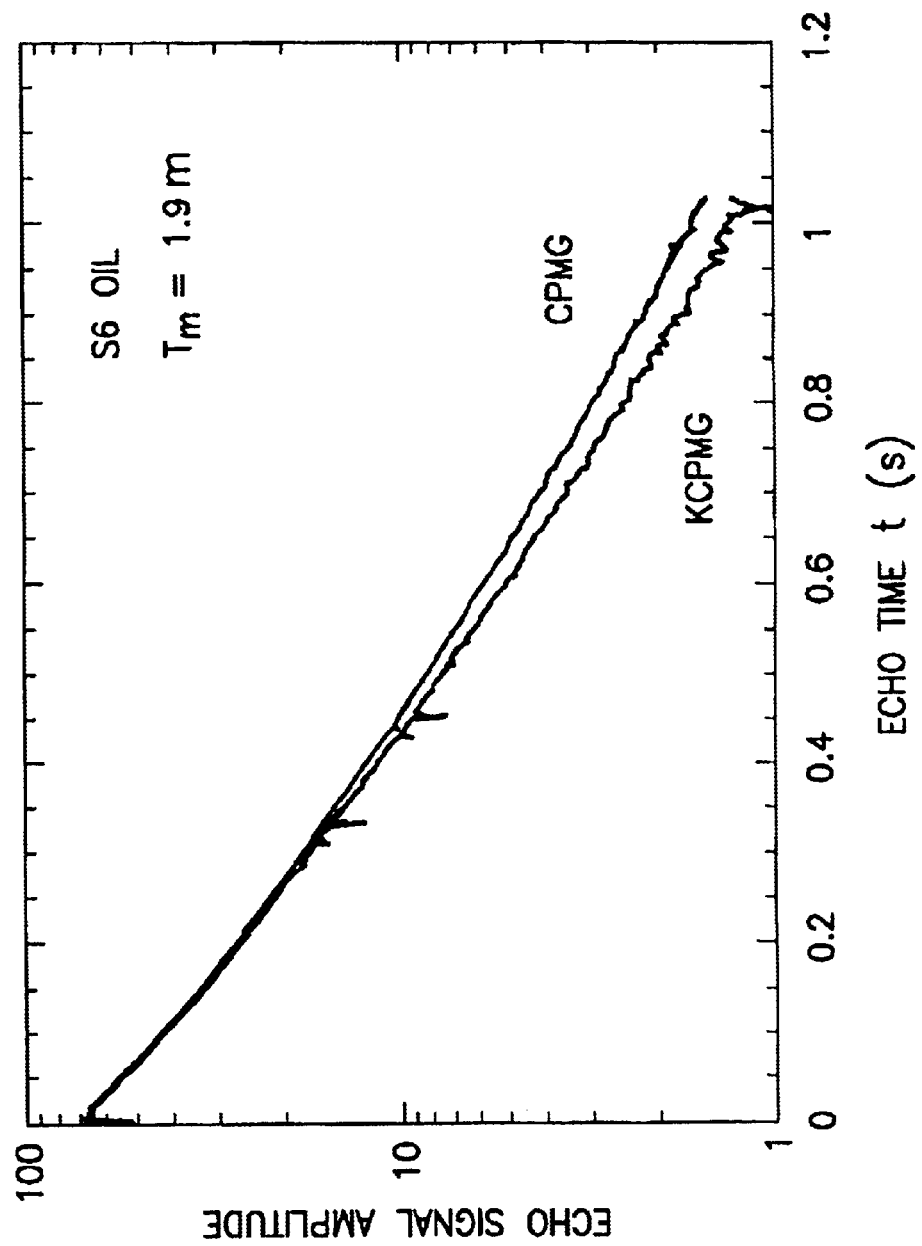
FIG. 3 is a graphical depiction of a comparison of KCPMG measurement for S6 oil at $T_m$ equal to 1.9 ms with CPMG data.

Similar experiments were performed on an oil sample (S6 oil), which is often used as a viscosity standard (obtained from Cannon Instrument Company, P.O. Box 16, State College, Pa.). FIG. 3 shows a comparison of KCPMG measurement for S6 oil at $T_m$ of 1.9 ms with CPMG data. In both cases, $T_{cp}=2$ ms and the magnetic field gradient was 10 G/cm. From the extra decay of the KCPMG data compared to the CPMG, the diffusion constant of the S6 oil was determined to be $0.82\times10^{-6}$ cm$^2$/s at 14 degrees C. The apparent glitches in the KCPMG data around 0.35 s and 0.4 s were caused by receiver problems. The experiments were performed on a Bruker AVANCE™ spectrometer at 85 MHz. The KCPMG echo signal is detected at the early echo and the amplitude is scaled up by factor of two in order to facilitate comparison with CPMG data in the figure. The CPMG and KCPMG data presented in FIG. 3 show a small additional decay in KCPMG compared to CPMG, in contrast to the much larger additional decay observed for water in FIG. 2. This is an indication of the much smaller diffusion constant of S6 oil, consistent with independent measurements using the pulsed field gradient method.

Restricted Diffusion

It is well-known that diffusion in porous media is restricted in the sense that the mean square displacement of molecules is less than that for the bulk fluid (see R. C. Wayne et al., "Nuclear-magnetic-resonance study of self-diffusion in a bounded medium," Phys. Rev. 151, 264 (1966), incorporated by reference herein in its entirety). It is often expressed as a reduced diffusion constant that is dependent on the diffusion time. For example, Mitra et al. in "Diffusion Propogator as a Probe of the Structure of Porous Media," Phys. Rev. Lett. 24, 3555 (1992) (incorporated by reference herein in its entirety) showed that such time-dependent diffusion constant can be used as a measure of the surface-to-volume ratio of materials. In addition, at long time when the molecular diffusion distance exceeds the characteristic length scale, such as the pore size, the diffusion constant reaches an asymptotic value that is a function of the connectivity of the pore system, $D(\infty)=D_0/F\phi$, where $\phi$ is the porosity of the sample and F is the formation factor, an important characteristic of porous materials. While brine saturated rocks were the subject of the examples below, this methodology is equally suited for other fluids in other porous media.

As will be shown below, the diffusion time in a KCPMG experiment is the time between the initial modulation and the detection of the N$^{th}$ echo, i.e. $\Delta \approx 2NT_{cp}$. For bulk fluids, because D is a constant independent of $\Delta$, it is difficult to prove that the measurements presented in the above are a measure of the true long-time displacements. In addition, while the analytical theory of the KCPMG sequence can be used to calculate in detail the effects of bulk diffusion, it is difficult to evaluate in detail the effects of restricted diffusion. As experimentally shown using the brine saturated rock samples below, the present methodology can be used to determine molecular displacement including diffusion and restricted diffusion.

Brine Saturated Rocks

KCPMG experiments on rocks were performed at low magnetic field of about 410 G in order to reduce the effects of internal field inhomogeneity due to susceptibility contrast. The Apollo™ NMR spectrometer (manufactured by Tecmag, Inc. of Houston, Tex.) operated at a Larmor frequency of 1.7 MHz. Rock samples were cylinders of 20 mm diameter and 38 mm length. The samples were placed in the fringe field of a superconducting magnet where the constant field gradient applied across the sample was 13.2 G/cm. The samples were saturated with brine similar to the borehole salinity. The $\pi/2$ and $\pi$ pulses are 12 and 24 $\mu$s long, respectively, exciting an approximately 5 mm slice of the sample perpendicular to the direction of the field gradient.

Figure 4A:
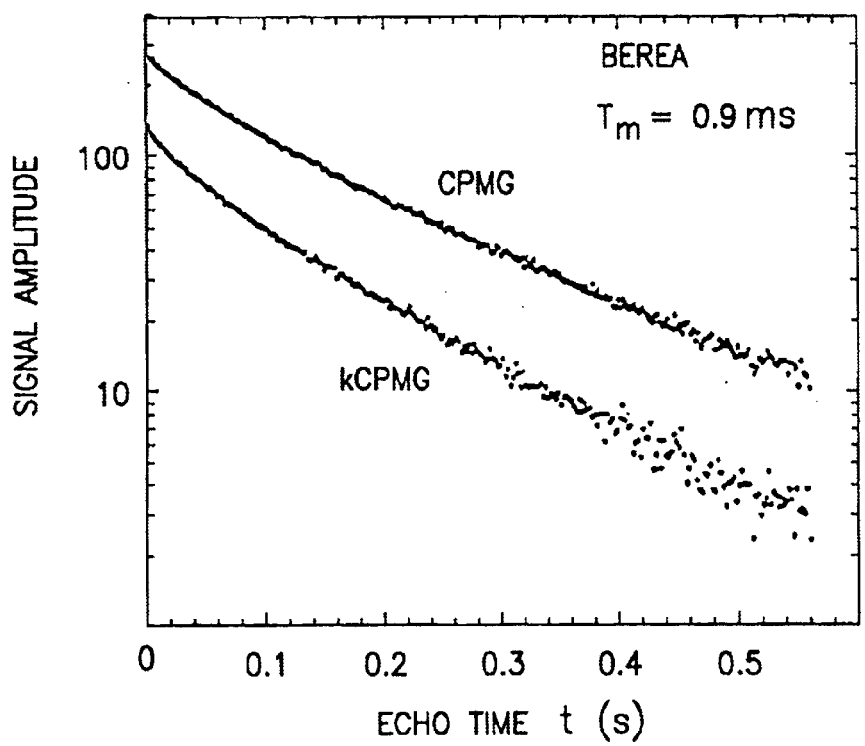
FIGS. 4(a)–(b) are graphical depictions of: (a) KCPMG and CPMG measurements of a Berea sample and (b) the mean square displacement extracted from (a).
Figure 4B:
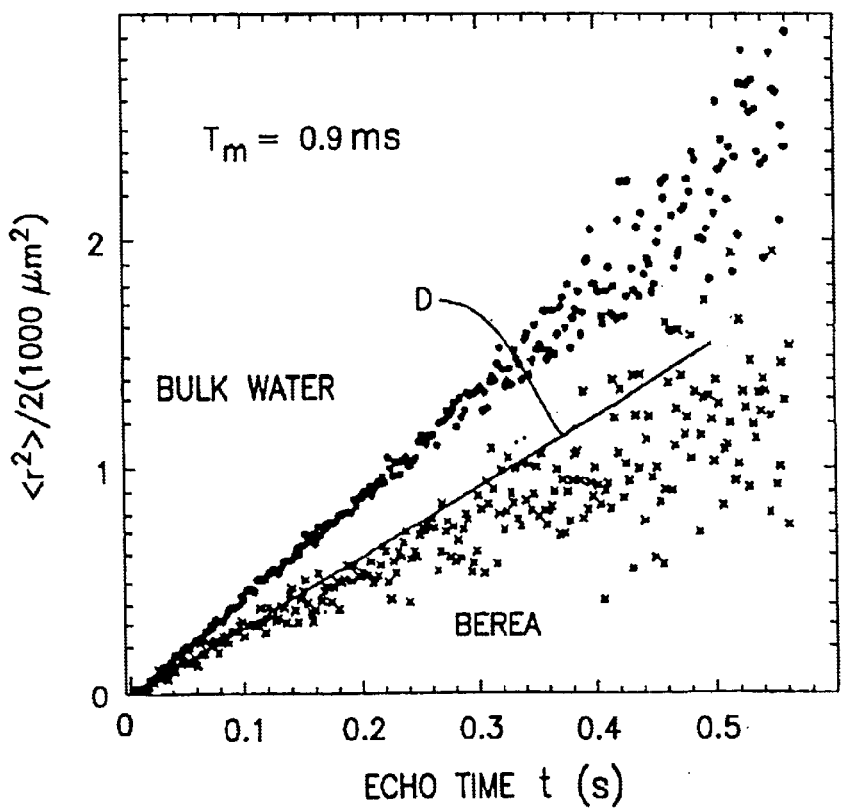

FIG. 4($a$) shows KCPMG measurements for a brine saturated Berea sandstone sample with $T_m=0.9$ ms, compared with the CPMG data where $T_{cp}=1.1$ ms. For this data, the magnetic field gradient was 13.2 G/cm. FIG. 4($b$) is a plot of the mean square displacement extracted from the KCPMG and CPMG measurements for water in the Berea sample (crosses) versus time. The data for bulk water (circles) were obtained under identical condition and are shown as a comparison. The line D is a fit to the displacement for Berea at early times showing that diffusion at long time is further reduced.

The decays of FIG. 4($a$) are approximately exponential, although there is a slight curvature at short times. This is consistent with a relatively narrow distribution of pore sizes in this type of rock. The mean square displacement of water due to diffusion versus time, obtained by $\log[S(K, t)/S(0, t)]/K^2$, is shown in FIG. 4($b$) and compared with that of bulk water. It is clear that the displacement in the rock is reduced compared to that in bulk water, a result consistent with the concept of restricted diffusion. It highlights the deviations of the Berea data at long time, indicating that the diffusion is being further slowed down at later times and that the diffusion cannot be described by a time-independent diffusion coefficient.

Figure 5A:
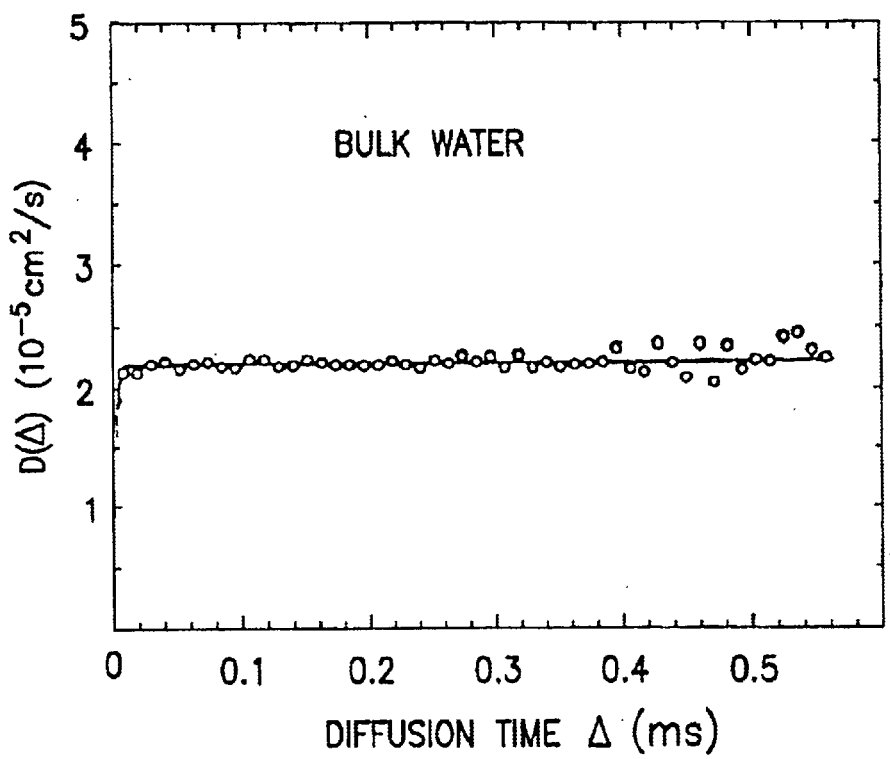
FIGS. 5(a)–(b) are graphical depictions of the time-dependent diffusion constant $D(\Delta)$ for: (a) the bulk water sample and (b) the Berea sample obtained from the KCPMG and CPMG data as a function of echo time.
Figure 5B:
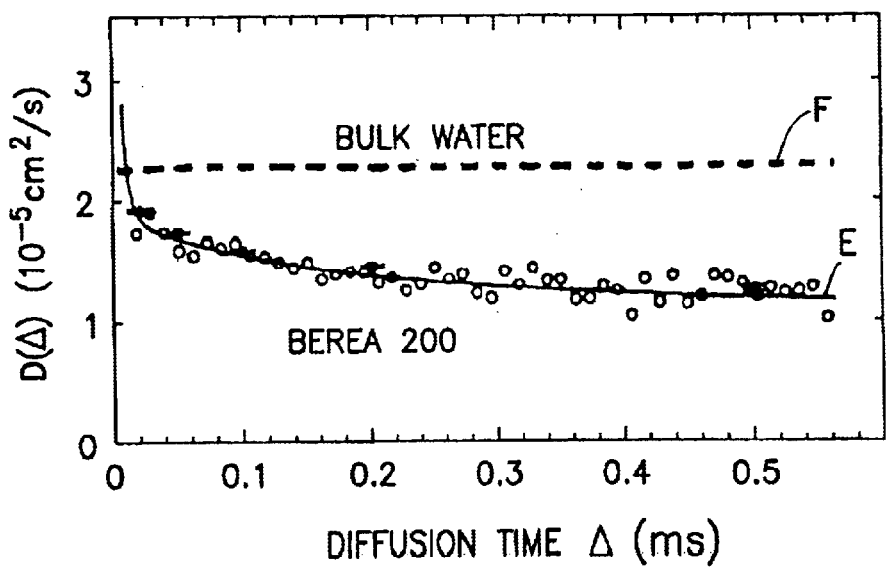

FIG. 5 shows the time-dependent diffusion constant $D(\Delta)$ for (a) the bulk water sample and (b) the Berea sample obtained from the KCPMG and CPMG data as a function of echo time. For KCPMG, the diffusion time $\Delta$ is $2NT_{cp}$. In FIG. 5($b$), the filled circles show $D(\Delta)$ obtained using conventional stimulated echo technique on the same sample. The results are consistent with the KCPMG results. The line E is obtained by Eq. 7 using the multi-exponential fits to the KCPMG and CPMG decay data. The corresponding measurement on bulk water is shown as the dotted line F for comparison. The gradual reduction of $D(\Delta)$ at long time is clear.

Because $D(\Delta)$ is expected to change with time smoothly, each point in FIGS. 5($a$) and ($b$) represent an average of five original data points. The gradual reduction of $D(\Delta)$ at long time is clear. In addition, D(t) by KCPMG is in complete agreement with the data obtained with stimulated echo experiments in a constant gradient.

At long diffusion time t when the molecules have diffused a distance larger than the pore spacing, $D(\Delta)$ approaches a constant, $D(\infty)=D_0/F\phi$. For samples with large pores, such as Berea sandstone, this limit can be reached at long time and is difficult to measure directly due to short spin relaxation time. For example, it takes 2 sec for water to diffuse 100 $\mu$m, which is much longer than the $T_1$ or $T_2$ relaxation times in Berea. However, in fine grained rocks such as mudstones, this limit can be reached within a time shorter than the relaxation time (see M. D. Hurlimann et al., "Dephasing of Hahn echo in rocks by diffusion in susceptibility-induced field inhomogeneities," Magn. Reson. Imaging 16, 535 (1998), incorporated by reference herein in its entirety).

Figure 6:
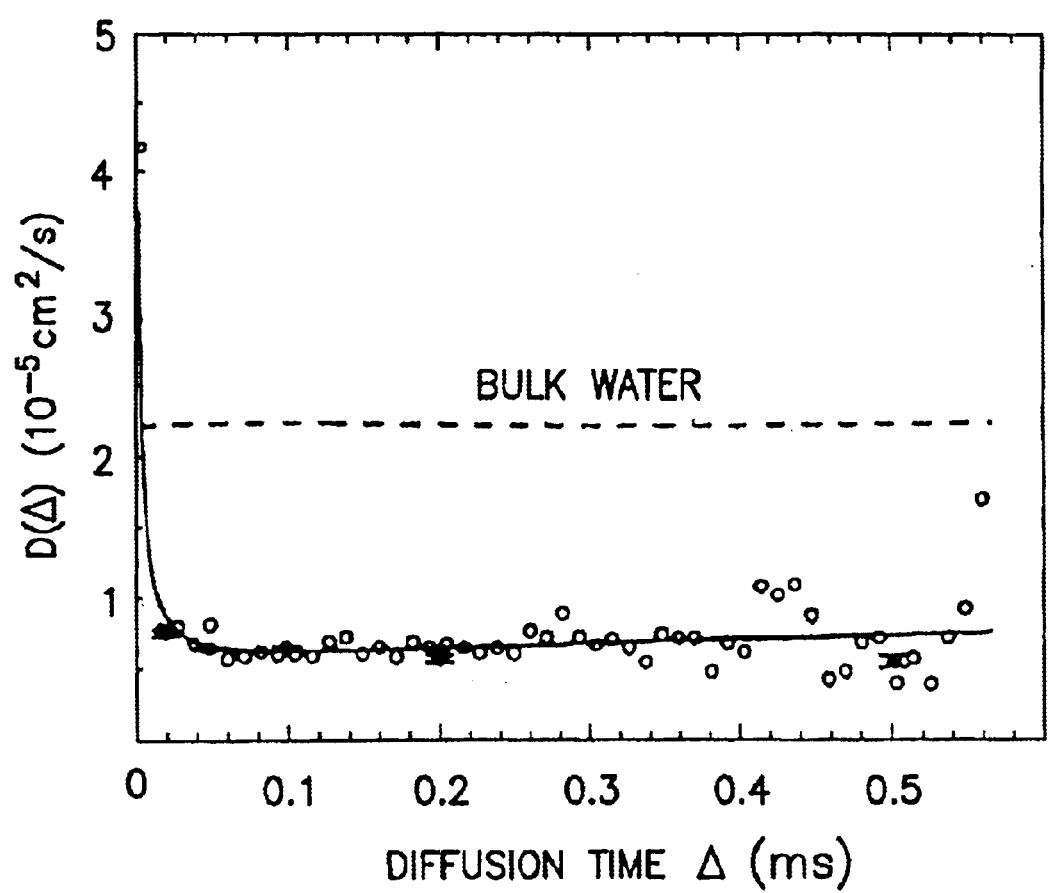
FIG. 6 is a graphical depiction of the time-dependent diffusion constant for water saturated carbonate rock obtained from the KCPMG and CPMG data as a function of echo time.

FIG. 6 shows the time-dependent diffusion constant $D(\Delta)$ obtained from the KCPMG and CPMG data as a function of echo time (open circles) for water saturated carbonate rock with pore sizes on the order of a few microns. For KCPMG, the diffusion time $\Delta$ is $2NT_{cp}$. Each data point represents the average of five original data points at nearby echo times. The noise is quite significant for echo time longer than 0.3 sec. $D(\Delta)$ obtained using stimulated echo technique on the same sample is shown as the black circles. The observed saturation of $D(\Delta)$ is consistent with the long time limit obtained independently from the measured formation factor and porosity. In FIG. 6 a long time limit is observed. The two data sets shown in FIG. 6 agree for times larger than 50 ms and D(t) saturates at about $0.7\times10^{-5}$ cm$^2$/s, consistent with the long time limit.

Presence of Grossly Inhomogeneous Fields

The experimental results shown in the sections above have demonstrated that Eq. 7 is a good ansatz for the measurements of the present invention and that it allows the extraction of the diffusion coefficient at multiple diffusion times in a single scan.

In grossly inhomogeneous fields, the KCPMG signal contains contributions from many different coherence pathways. It would be natural to expect that contributions from some of the coherence pathways do not follow the simple relationship of Eq. 7. In fact, Eq. 7 is a valid approximation for some of the coherence pathways. For example, let us consider the ninth echo, i.e., N=9, and one such coherence pathway is Q=(+++++-----). This is equivalent to a spin echo with an effective pulse spacing between the $\pi/2$ and $\pi$ pulse of $9T_{cp}$. Thus, this coherence pathway contributes to the KCPMG signal (summing contributions from positive and negative values of $T_m$) as $$S_Q = e^{-\frac{2}{3}D(\gamma G)^2(9T_{cp}+\delta)^3} + e^{-\frac{2}{3}D(\gamma G)^2(9T_{cp}-\delta)^3} \quad (11)$$

$$= 2e^{-\frac{2}{3}D(\gamma G)^2(9T_{cp})^3} e^{-DK^2 18T_{cp}} \times \cosh\left\{2K^2D\left[\frac{(9T_{cp})^2}{\delta}+\frac{\delta}{3}\right]\right\}$$

The cosh factor for the above pathways may not be approximated by 1 and the contribution from this pathway can deviate from the ansatz in Eq. 7. However, coherence pathways such as Q=(+++++-----) do not contribute much to the CPMG and KCPMG echoes, because with the pulse sequences presented herein they are ineffectively excited and do not have large degeneracies. A detailed analysis of CPMG coherence pathways and their classification has shown that the main contribution to the CPMG signals comes from two classes of coherences, the direct echo and the so-called singly stimulated echoes. The term singly stimulated echo refers to those pathways with no consecutive + or − present. For these pathways, the spatial modulation of the phase is usually characterized by wave vectors with a magnitude less than $\gamma GT_{cp}$. The basic segment of the singly stimulated coherence pathway is $$-\underbrace{0\ldots0}_{s_1}+, \text{ and } +\underbrace{0\ldots0}_{s_2}- \quad (12)$$

where $s_1$ is the number of q=0 in such segments. The direct echo can be seen as the special case with $s_1$=0. Contributions from these two classes account for about 95% of the CPMG signal. Furthermore, the average length of such segments has been found to be very short for CPMG, $<s_1>$ is approximately less than 2. These results illustrate a fundamental characteristic of the coherence pathways in CPMG and related sequences; namely, that the basic segments are the direct spin echo segments, +−, and short singly stimulated segments with $s_1\sim 2$. The CPMG signals should be attributed primarily to the pathways formed by these short segments as the repeating units.

For a singly stimulated segment, +0 . . . 0− with $s_1$ zeros, using the Hahn's formula for stimulated echo attenuation (see E. L. Hahn, "Spin Echoes," Phys. Rev. 80, 580 (1950), incorporated by reference herein in its entirety), the decay component (summing both positive and negative $T_m$) is:

$$S_Q = e^{\frac{-D(\gamma G)^2(T_{cp}-\delta)^2(2T_{cp}-2\delta+6s_1 T_{cp})}{3}} + e^{\frac{-D(\gamma G)^2(T_{cp}+\delta)^2(2T_{cp}+2\delta+6s_1 T_{cp})}{3}} \quad (13)$$

$$= 2e^{-D(\gamma G)^2\left(\frac{2}{3+2s_1}\right)T_{cp}^3} \times e^{-DK^2(2+2s_1)T_{cp}} \times \cosh\left(D(\gamma G)^2\left((2+4s_1)T_{cp}^2\delta+\frac{2\delta^3}{3}\right)\right)$$

The first term, $\exp[-D(\gamma G)^2(\frac{2}{3}+2s_1)T_{cp}^3]$, is the same for the CPMG contribution. The second term $\exp[-DK^2(2+2s_1)T_{cp}]$ is the KCPMG factor. When $s_1$ is small and $D(\gamma G)^2T_{cp}^3$ is small, the cosh term approximates 1 to the second order. Thus, this contribution is consistent with Eq. 7.

KCPMG to Monitor other Processes

Because KCPMG is capable of monitoring molecular displacement as a function of echo time, it may also be used to monitor coherent movement of molecules, such as in a flowing fluid. In particular, because this experiment measures displacement as a function of time, it can be used to obtain velocity and acceleration in a non-stationary flow.

In general, KCPMG is capable of monitoring evolution of magnetization and it may be useful to study other processes, for example, magnetization transfer via chemical exchange. This process is commonly measured by first perturbing the spin system out of equilibrium and then monitoring its evolution as a function of time, $\Delta$. Usually, experiments have to be repeated for different $\Delta$ in order to characterize the dynamics over a range of time scales. Using KCPMG (in this case without field gradient), the entire $\Delta$-dependence can be obtained in one or a few scans. For example, consider a two-proton system with a difference in resonant frequency f due to chemical shifts. Let $T_m=\pm\frac{1}{2}$ f, then the spins of the two protons will point to the opposite directions at the beginning of the CPMG portion of KCPMG (Eq. 3). Then, KCPMG echoes will reflect the evolution of the initial state with two opposite-pointing spins. The relative short acquisition window ($2T_{cp}$) will limit the spectral resolution.

The methodology of determining magnetization transfer by chemical exchange is similar to the methods discussed above with respect to molecular displacement; however, a strong magnetic field gradient is not required and the sequence is design to induce a chemical shift modulation rather than a spatial modulation. Accordingly, in an alternative embodiment, magnetization transfer by chemical exchange is measured by: applying a sequence of oscillating magnetic field pulses to the sample wherein the sequence includes a first portion followed by a second portion, wherein said first portion induces a chemical shift modulation of the sample and the second portion monitors the evolution of the modulation; detecting magnetic resonance signals from the sample; and analyzing the detected signals to determine the magnetization transfer of the sample The uncertainties in the extracted value of the time dependent diffusion coefficient from KCPMG depends on time. At early time, the diffusion effect is small, possibly resulting in large errors. At very long times, the relative attenuation is large, but the overall amplitudes are very small. This may lead again to large errors.

General KCPMG Theory

This section presents the theory of KCPMG for bulk diffusion by analyzing the contributing coherence pathways similar to those described for CPMG previously. While this theory is presented specifically for the pulse sequence in Eq. 3, it may be adapted for other sequences.

Coherence Pathways for CPMG

The following notations will be used in defining three states of spin magnetization of an ensemble of spin-½ nuclei, $M_0$, $M_-$ and $M_+$:

$$M_0 = M_z \quad (15)$$
$$M_+ = M_x + iM_y$$
$$M_- = M_x - iM_y$$

These states are marked by q which can be 0, +1, and −1, (or 0, + and −), respectively. The RF pulses rotate the magnetization vector and thus change q, $$M(t_p) = R \cdot M(0) \quad (16)$$

Here, $M(0)$ and $M(t_p)$ are the magnetization vectors before and after the pulse and the pulse duration is $t_p$. R depends on the Larmor frequency offset from the RF frequency $\omega_{RF}$, $\Delta\omega_0 = \gamma|B_0| - \omega_{RF}$, $\omega_1$, and $t_p$. Then, the nutation frequency is $\Omega = \sqrt{\omega_1^2 + \Delta\omega_0^2}$ where $\omega_1 = \gamma B_1/2$, and the tipping angle is $\Omega t_p$. The matrix elements, $R_{1,m}$, are:

$$R_{+,+} = R^*_{-,-} = \frac{1}{2}\left\{\left(\frac{\omega_1}{\Omega}\right) + \left[1 + \left(\frac{\Delta\omega_0}{\Omega}\right)^2\right]\cos(\Omega t_p)\right\} + i\left(\frac{\Delta\omega_0}{\Omega}\right)\sin(\Omega t_p) \quad (17)$$

$$R_{0,0} = \left(\frac{\Delta\omega_0}{\Omega}\right)^2 + \left(\frac{\omega_1}{\Omega}\right)^2 \cos(\Omega t_p) \quad (18)$$

$$R_{+,0} = R^*_{-,0} = \frac{\omega_1}{\Omega}\left\{\frac{\Delta\omega_0}{\Omega}[1 - \cos(\Omega t_p)] - i\sin(\Omega t_p)\right\}e^{+i\phi} \quad (19)$$

$$R_{0,+} = R^*_{0,-} = \frac{\omega_1}{\Omega}\left\{\frac{\Delta\omega_0}{\Omega}[1 - \cos(\Omega t_p)] - i\sin(\Omega t_p)\right\}e^{-i\phi} \quad (20)$$

$$R_{+,-} = R^*_{-,+} = \frac{1}{2}\left(\frac{\omega_1}{\Omega}\right)^2 + [1 - \cos(\Omega t_p)]e^{+i2\phi} \quad (21)$$

The rotations for the $\pi/2$ and $\pi$ pulses are labeled as $L_{q,q'}$ and $\Lambda_{q,q'}$, respectively.

A coherence pathway is characterized by a series of numbers, $Q_N \equiv (q_0, q_1, \ldots, q_N)$, where $q_0$ is the magnetization state before the first $\pi$ pulse and N is the echo number. Y.-Q. Song in "Categories of coherence pathways in the CPMG sequence," J. Magn. Reson. 157, 82 (2002) (incorporated by reference herein in its entirety) has presented a classification of the major coherence pathways showing the importance of two classes of coherences, the direct spin echo (SE) and the stimulated echo (STE).

In the absence of spin relaxation, the $N^{th}$ echo signal is obtained from a sum over all coherence pathways $$\left(M(N) = \sum_{Q_N} M_{Q_N}\right)$$

where each term can be written as a product of two factors:

$$M_{Q_N} = A_Q \cdot S_Q \quad (22)$$

$$= \left(L_{0,q_0}\prod_{l=1}^{N}\Lambda_{q_l,q_{l-1}}\right)\left(\exp\left(i\sum_{l=0}^{N}q_l\phi_l\right)\right)$$

Here, $L_{qq'}$ and $\Lambda_{qq'}$ are matrix elements of the $\pi/2$ and $\pi$ pulses and $A_Q$ is identical for KCPMG and CPMG for the same coherence pathway. Also, $A_Q$ depends on the frequency offset and the RF power. $\phi_l$ is the random phase factor due to diffusion between pulse l and l+1 in the presence of magnetic field gradients. The angle brackets $\langle \ldots \rangle$ represent an ensemble average of the random phase factors, $\phi_0, \phi_1, \phi_2, \ldots, \phi_N$. $S_Q$ does not depend on frequency offset. For unrestricted diffusion, this contribution can be written as $$S_Q = \exp\left(-\frac{2}{3}\eta_{Q_N}\gamma^2 G^2 D T_{cp}^3 N\right) \quad (23)$$

where $\eta_{Q_N}$ is the enhancement of the decay rate for $Q_N$ compared to that of the direct echo pathway (see M. D. Hurlimann, "Diffusion and relaxation effects in general stray field NMR experiments," J. Magn. Reson. 148, 367 (2001) and D. E. Woessner, "Effects of diffusion in nuclear magnetic resonance spin-echo experiments," J. Chem. Phys. 34, 2057 (1961), incorporated by reference herein in their entireties). Also, G is the applied field gradient, D is the bulk diffusion constant, and $T_{cp}$ is half of the time between adjacent $\pi$ pulses.

Analytical Results for Early KCPMG Echoes

For the echoes after the first and second $\pi$ pulses, the coherences are limited to Hahn echoes and stimulated echoes. These diffusion effects have been calculated by Hahn in "Spin Echoes," Phys. Rev. 80, 580 (1950).

For echoes after first $\pi$ pulse, contribution from direct echo coherence, CPMG:

$$M_1 = e^{-\frac{2}{3}D(\gamma G)^2 T_{cp}^3} \quad (24)$$

and KCPMG (adding the signals for $T_m > 0$ and $T_m < 0$):

$$M_1 = e^{-\frac{2}{3}D(\gamma G)^2(T_m+T_{cp})^3} + e^{-\frac{2}{3}D(\gamma G)^2(T_m-T_{cp})^3} \quad (25)$$

$$= e^{-\frac{2}{3}\alpha - 2D(\gamma G)^2 T_m^2 T_{cp}} \cdot \left[e^{-D(\gamma G)^2\left(T_{cp}^2 T_m - \frac{T_m^3}{3}\right)} + e^{D(\gamma G)^2\left(T_{cp}^2 T_m + \frac{T_m^3}{3}\right)}\right]$$

$$\approx e^{-\frac{2}{3}\alpha - 2DK^2 T_{cp}}[2 + O(\alpha^2)] \quad (26)$$

where $K = \gamma G T_m$, $\alpha = D(\gamma G)^2 T_{cp}^3$ and $\alpha$ is assumed to be much less than 1. $O(\alpha^2)$ denotes a term second order in $\alpha$.

The coherence pathways in CPMG and KCPMG for these echoes are identical, thus the matrix elements ($A_Q$) determining the weight of these pathways are the same. Hence, the ratio of the KCPMG data and the CPMG data is approximately $\exp[-K^2 D \cdot 2T_{cp}]$.

For echoes after the second $\pi$ pulse, CPMG:

$$SE: e^{-\frac{4}{3}\alpha} \tag{27}$$

$$STE: e^{-\frac{8}{3}\alpha} \tag{28}$$

and KCPMG (where $T_m < 0$)

$$SE: e^{-\frac{2}{3}D(\gamma G)^2(T_{cp}-T_m)^3} e^{-\frac{2}{3}(\gamma G)^2(T_{cp}+T_m)^3} = e^{-\frac{4}{3}\alpha - D(\gamma G T_m)^2 4 T_{cp}} \tag{29}$$

$$STE: e^{-\frac{D(\gamma G)^2(T_{cp}-T_m)^2(8T_{cp}-2T_m)}{3}} \tag{30}$$

and KCPMG (where $T_m > 0$)

$$SE: e^{-\frac{2}{3}D(\gamma G)^2(T_{cp}-T_m)^3} e^{-\frac{2}{3}(\gamma G)^2(T_{cp}-T_m)^3} = e^{-\frac{4}{3}\alpha - D(\gamma G T_m)^2 4 T_{cp}} \tag{31}$$

$$STE: e^{-\frac{D(\gamma G)^2(T_{cp}+T_m)^2(8T_{cp}+2T_m)}{3}} \tag{32}$$

Combining signals from positive and negative $T_m$, $$SE: 2e^{-\frac{4}{3}\alpha - DK^2 4 T_{cp}} \tag{33}$$

$$STE: e^{-\frac{8}{3}\alpha - DK^2 4 T_{cp}}[2 + O(\alpha)^2] \tag{34}$$

The frequency spectra of these coherence pathways are determined by the matrix elements ($A_Q$). The amplitudes of the two coherence pathways depend on the RF pulses and the frequency filtering in detection. Let $A_{SE}$ and $A_{STE}$ denote these amplitudes, thus the KCPMG signal can be expressed as $$M_2 \approx 2A_{SE} e^{-\frac{4}{3}\alpha - DK^2 4 T_{cp}} + 2A_{STE} e^{-\frac{8}{3}\alpha - DK^2 4 T_{cp}} = \tag{35}$$

$$e^{-DK^2 4 T_{cp}} \times \left[2A_{SE} e^{-\frac{4}{3}\alpha} + 2A_{STE} e^{-\frac{4}{3}\alpha}\right]$$

where the factor between the square brackets is precisely the signal for the second CPMG echo.

KCPMG Echoes After Many $\pi$ Pulses

For the KCPMG sequence, for example, Eq. 3, the contribution from a coherence pathway Q is a product of two factors, $$M_{Q_N} = A_Q \cdot S_Q^K \tag{36}$$

where $A_Q$ is the product of the matrix elements associated with the RF pulses and is identical to the corresponding term for CPMG. The factor $S_Q^K$ is the diffusion decay factor that include the initial magnetization modulation $\exp(\pm i\Delta\omega_0|T_m|)$. The $$S_Q^K$$

factor is, in general, different from the corresponding term for CPMG. In order to understand $$S_Q^K$$

it is useful to introduce for each coherence pathway the instantaneous wavevector k(t) in analogy to the approach in magnetic resonance imaging:

$$k(t) = \gamma G \int_0^t q(t')dt' \tag{37}$$

where q(t') is the instantaneous value of q that is piecewise constant between pulses. The diffusive attenuation for a given coherence pathway and unrestricted diffusion can then generally be written as $$S_Q^K = \exp\left\{-D \int_0^T k(t)^2 dt\right\} \tag{38}$$

where time t=0 is defined at the beginning of the sequence (Eq. 3) and T is the echo time. The inclusion of $T_m$ in the initial pulse spacing of the KCPMG sequence leads to a shift of the instantaneous wavevector of K relative to that in the CPMG sequence. k(t) denotes the instantaneous wavevector for the CPMG sequence. Up to corrections of order $\exp(D\gamma^2 G^2 \delta^3)$, the diffusive attenuation can be written as:

$$S_Q^K(K, t) \approx \exp\left\{-D \int_{T_m}^{T_m + 2NT_{cp}} [k(t) + K]^2 dt\right\} = \tag{39}$$

$$S_Q(2NT_{cp}) \times \exp\{-DK^2 \cdot 2NT_{cp}\} \times \exp\left\{-2DK \int_{T_m}^{2NT_{cp}} k(t) dt\right\}$$

The integral limits $T_m$ and $T_m + 2NT_{cp}$ correspond to the beginning and the echo position of the CPMG sequence. This factorization thus facilitates comparison with the CPMG sequence, for instance, $S_Q(2NT_{cp})$ is the decay factor for CPMG. This expression shows that for symmetrical coherence pathways such as the direct echo, $$\int_0^t k(t) dt = 0,$$

and the last term can be replaced by 1. In this case, the ansatz for the KCPMG sequence is recovered. However, for a general coherence pathway, the last term is not exactly 1 and the ansatz becomes an approximation. The key question is whether the signal is dominated by contributions from coherence pathways, where the correction term is small, or not. The experimental results indicate that the ansatz is indeed a good approximation. Support may be found in numerical calculations, where the weight and diffusive attenuation is calculated for all coherence pathways that contribute signal up to the 15th echoes. Similar to the treatment of CPMG echoes, the diffusion factor $$S_Q^K$$

is parametrized as $$S_Q^K = \exp\left(-\frac{2}{3}\eta_{Q_N}\gamma^2 G^2 D T_{cp}^3 N\right) \tag{40}$$

Figure 7:
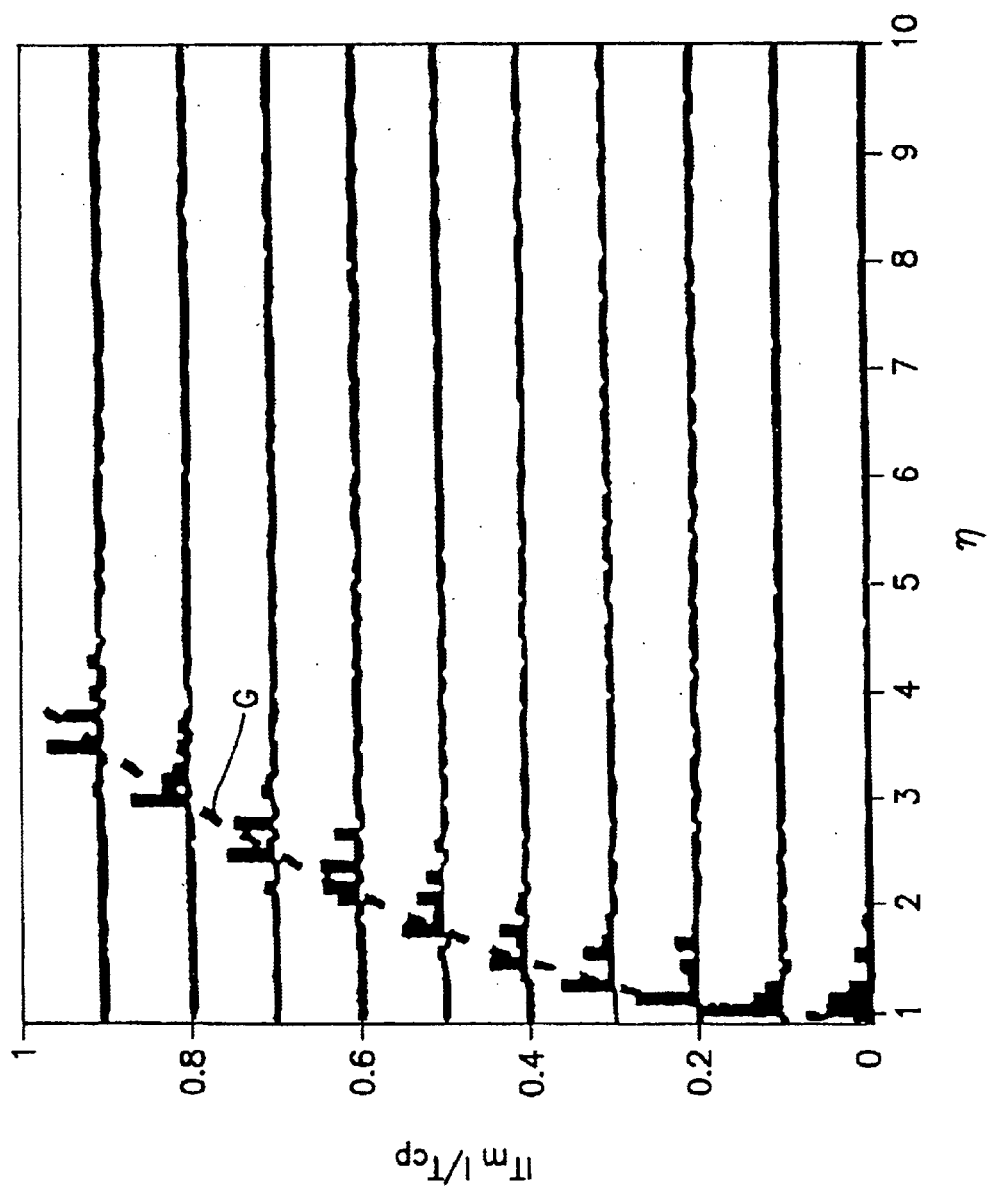
FIG. 7 is a graphical depiction of calculated diffusion decay factor η for the coherence pathways for the 15$^{th}$ echo as $|T_m|/T_{cp}$ increases.
Figure 8:
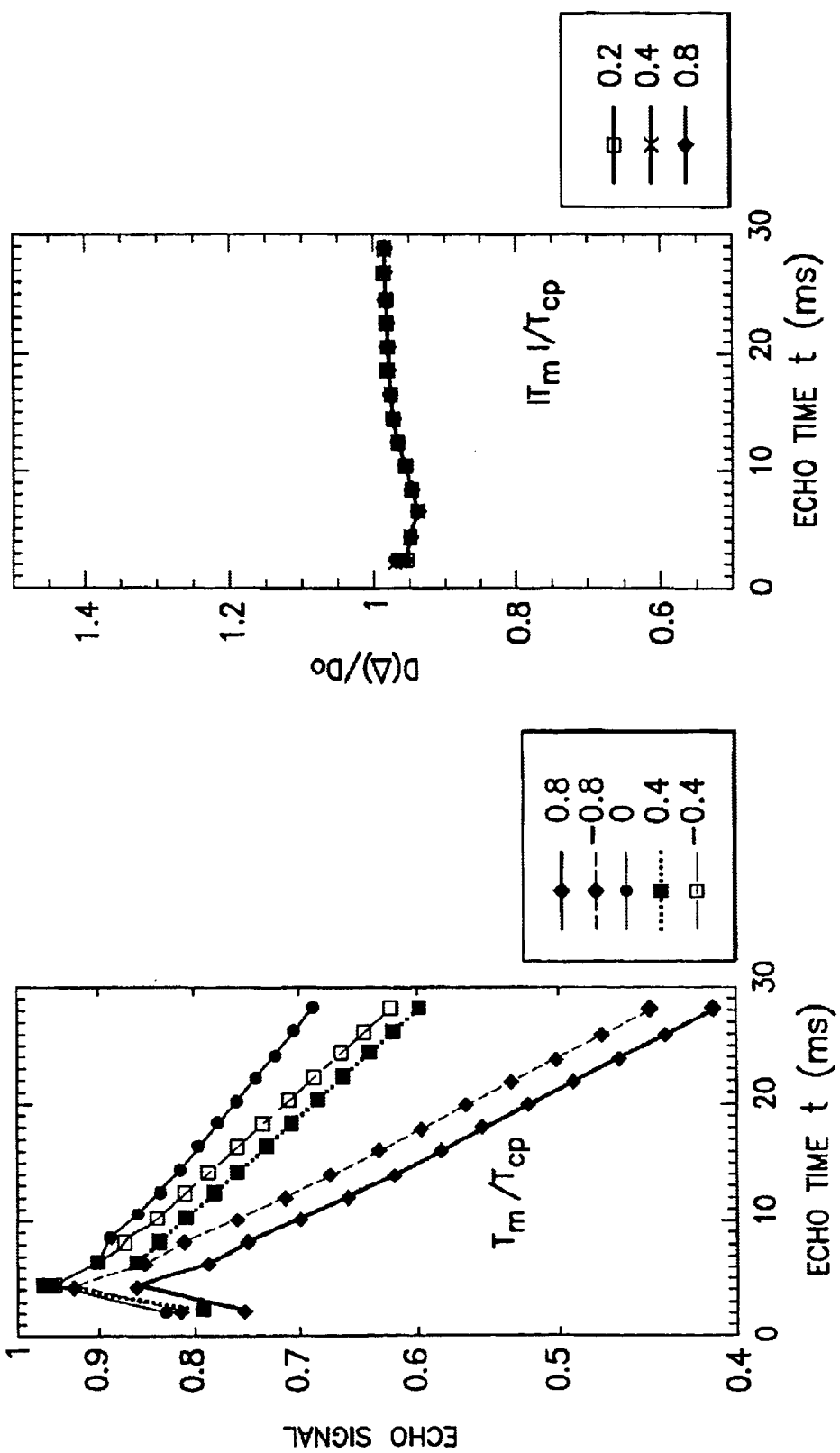
FIGS. 8(a)–(b) are graphical depictions of: (a) calculated KCPMG echo amplitudes of the first 14 echoes and (b) time-dependent diffusion constant calculated from the KCPMG echoes using Eq. 7 (as described below).

The numerical results are summarized below. FIG. 7 shows the calculated diffusion decay factor $\eta$ for the coherence pathways of the 15th echo, as $|T_m|/T_{cp}$ increases (i.e., summing the contribution from the positive and negative $T_m$). The enhancement of $\eta$ as $|T_m|/T_{cp}$ increases is consistent with the behavior of Eq. 7, as indicated by the line G. As $|T_m|/T_{cp}$ increases, the diffusion rate for the major coherence pathways increases and the increase is approximately proportional to $K^2$, consistent with Eq. 7. The KCPMG echoes has been calculated by summing all coherence pathways, then obtained the signal intensity using a filter that is of the shape of asymptotic CPMG echo shifted to the corresponding KCPMG echo positions. These echo amplitudes are used to calculate D(t) by Eq. 7, and the results are shown in FIGS. 8(a) and (b). FIG. 8 shows (a) calculated KCPMG echo amplitudes of the first 14 echoes, for $T_m/T_{cp}=$ ±0.8,±0.4 and; (b) time-dependent diffusion constant calculated from above KCPMG echoes using Eq. 7. The parameters used are: G=40G/cm, $T_{cp}$=1 ms, and D=2.3×10$^{-5}$cm$^2$/s.

Accordingly, it has been presented herein a method to extend the CPMG sequence to detect molecular displacement at many time points in one scan of the sequence. The essence of the present invention is a modification to the CPMG sequence wherein the initial magnetization is modulated and the evolution of such modulation is observed with the CPMG π pulse train. Despite the complexity of the coherence pathways in CPMG and KCPMG, we provide an intuitive understanding of the sequence. This new method enables a rapid measurement of diffusion in bulk fluids and most importantly in porous media where the diffusion process is restricted by the pore geometry. This method might be particularly useful for applications of hyperpolarized gases, such as xenon and helium, or other non-equilibrium magnetization sources where it is difficult to maintain a sufficiently stable supply for multiple experiments. Using the KCPMG concept, only a few scans may be needed to obtain results for many diffusion times.

Exemplary Apparatus

Figure 9:
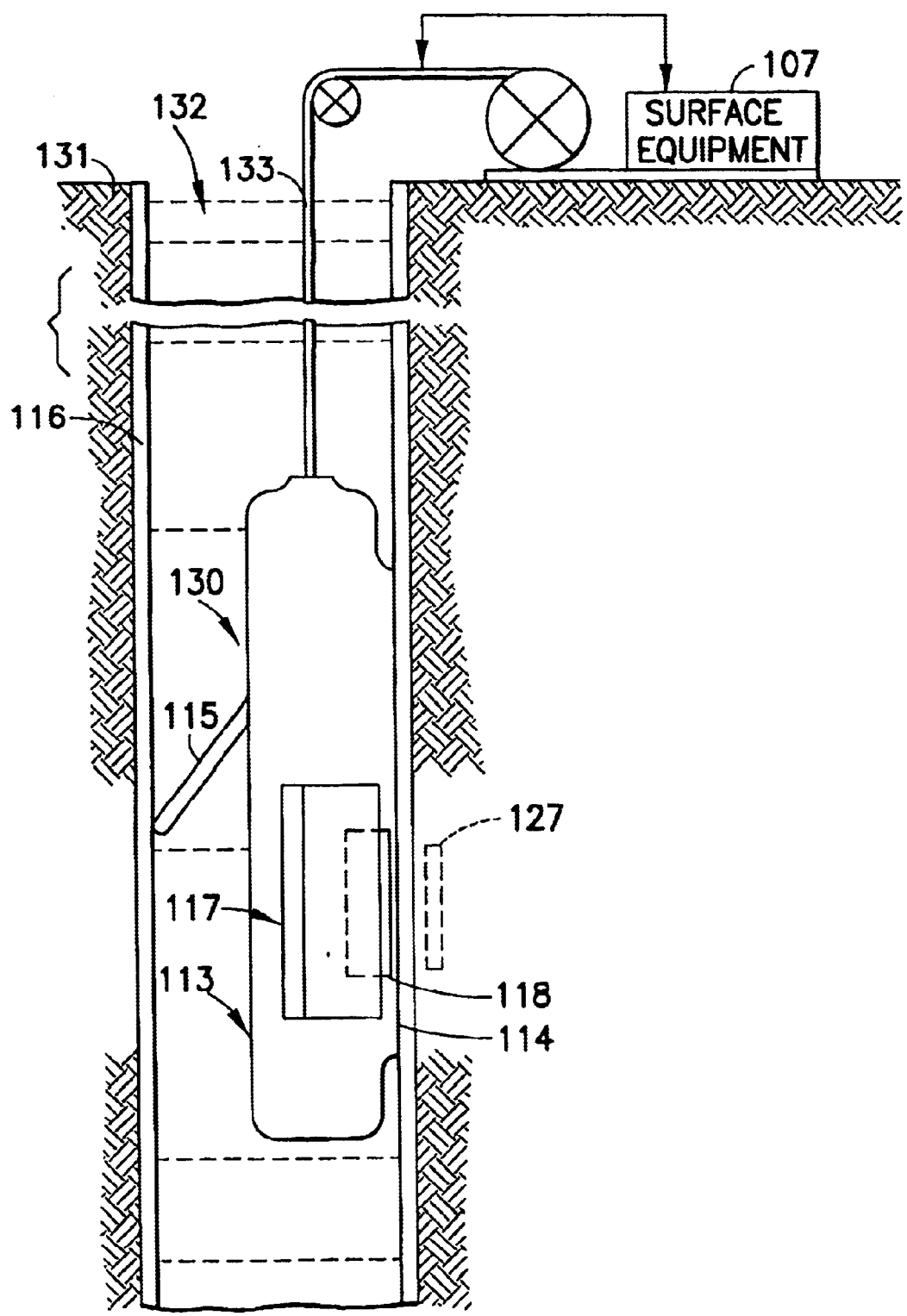
FIG. 9 is a schematic diagram, partially in block form, of one embodiment of a well logging apparatus that can be used in implementing methods according to the invention in a borehole environment.

The methods of the invention may be practiced in a laboratory setting or in a downhole environment, such as with a well logging device. FIG. 9 shows an apparatus that can be utilized for practicing embodiments of the invention to investigate subsurface formations 131 traversed by a borehole 132. A magnetic resonance investigating apparatus or logging device 130 is suspended in the borehole 132 on an armored cable 133, the length of which substantially determines the relative depth of the device 130. The length of cable 133 is controlled by suitable means at the surface such as a drum and winch mechanism. Surface equipment, represented at 107, can be of conventional type, and can include a processor subsystem that communicates with all the downhole equipment. It will be understood that some of the processing can be performed downhole and that, in some cases, some of the processing may be performed at a remote location. Also, while a wireline is illustrated, alternative forms of physical support and communicating link can be used, for example in a measurement-while-drilling or logging-while-drilling system, in practicing the methods of the invention.

As described, for example, in U.S. Pat. Nos. 5,055,787, 5,055,788, and 5,153,514, the magnetic resonance logging device 130 can have a face 114 to intimately contact the borehole wall. The borehole wall may have a mudcake 116 thereon. A retractable arm 115 is provided which can be activated to press the body of the tool 113 through the mudcake against the borehole wall during a logging run, with the face 114 pressed against the wall's surface. Although the tool 113 is shown as a single body, the tool may alternatively include separate components such as a cartridge, sonde or skid, and the tool may be combinable with other logging tools.

The logging device includes, for example, a permanent magnet or permanent magnet array 117, which may be made of a samarium-cobalt-magnetic material, and one or more RF antennas 118. The investigation region, or sensitivity zone, represented generally at 127, is a region in the formation in which the static magnetic field is generally uniform, although this is not necessarily required for operation in accordance with the invention. Some embodiments of the invention may take advantage of inherent non-uniformity in the static magnetic field to generate a static magnetic field gradient within the investigation region 127. In other embodiments, pulsed magnetic field gradients may be used to generate or enhance a magnetic field gradient within the investigation region 127. U.S. Pat. No. 5,796,252, for example, which is incorporated herein by reference, describes various embodiments of an antenna that can be incorporated into logging devices of the invention and used to produce pulse field gradients in the investigation region 127. It will be understood that other suitable tool configurations can be utilized for practicing the invention.

While the invention has been described herein with reference to certain examples and embodiments, it will be evident that various modifications and changes may be made to the embodiments described above without departing from the scope and spirit of the invention as set forth in the claims.

What is claimed is:

1. A method of measuring the molecular displacement of a fluid comprising:

a) applying a strong magnetic field gradient to said fluid;

b) applying a sequence of oscillating magnetic field pulses to said fluid wherein said sequence includes a first portion followed by a second portion, wherein said first portion spatially modulates the magnetization state of the fluid and said second portion monitors the evolution of said modulation;

c) detecting magnetic resonance signals from said fluid; and d) analyzing said detected signals to determine the molecular displacement of said fluid.

2. The method of claim 1, wherein said strong magnetic field gradient is grossly inhomogeneous.

3. The method of claim 1, wherein analyzing said detected signals includes determining the diffusion of said fluid.

4. The method of claim 1, wherein analyzing said detected signals includes determining the velocity of said fluid.

5. The method of claim 1, wherein analyzing said detected signals includes determining the acceleration of said fluid.

6. The method of claim 1, wherein said fluid is contained in a porous media.

7. The method of claim 6, wherein said porous media is a region of earth formation.

8. The method of claim 1, wherein said strong magnetic field gradient is greater than $1/\gamma L t_\pi$, where γ is the gyromagnetic ratio of the nuclei of said fluid, L is the sample length along the gradient direction, and $t_\pi$ is the time duration of the π pulse.

9. The method of claim 1, wherein said oscillating sequence is comprised of:

$$\frac{\pi}{2} - T_m - T'_{cp} - [\pi - 2T_{cp}]_N$$

where $$T_{cp}' = T_{cp} - \frac{2t_{\frac{\pi}{2}}}{\pi},$$

$T_{cp}$ is a waiting period, $T_m$ is a waiting period where $|T_m|<T'_{cp}$, and $t_{\pi/2}$ is the duration of the $\pi/2$ pulse.

10. The method of claim 1, wherein said sequence produces more than one echo.

11. The method of claim 1, further comprising repeating (b) and (c) one or more times.

12. The method of claim 1, wherein said sequence of oscillating magnetic field pulses is comprised of:

$$\pi/2-\delta-\pi/2-T_d-\pi/2-T_{cp}-[\pi-2T_{cp}]_n$$

wherein $T_d$ is the initial diffusion time, $T_{cp}$ is a waiting period.

13. The method of claim 1, further comprising applying a CPMG sequence to said fluid and detecting magnetic resonance signals.

14. The method of claim 1, wherein said sequence of oscillating magnetic field pulses is comprised of:

$$\pi/2-\delta/2-\theta_1-\delta/2-\theta_2-T_{cp}-[\pi-2T_{cp}]_n$$

wherein $T_{cp}$ is a waiting period.

15. A method of measuring the molecular displacement of a fluid through a porous media comprising:
 a) applying a strong magnetic field gradient to said fluid;
 b) applying a sequence of oscillating magnetic field pulses to said fluid wherein said sequence includes a first portion followed by a second portion, wherein said first portion spatially modulates the magnetization state of the fluid and said second portion monitors the evolution of said modulation;
 c) detecting magnetic resonance signals from said fluid; and
 d) analyzing said detected signals to determine the restricted diffusion of said fluid through said porous media.

16. The method of claim 15, wherein said porous media is a region of earth formation.

17. The method of claim 15, wherein said strong magnetic field gradient is greater than $1/\gamma Lt_\pi$, where $\gamma$ is the gyromagnetic ratio of the nuclei of said fluid, L is the sample length along the gradient direction, and $t_\pi$ is the duration of the $\pi$ pulse.

18. The method of claim 15, wherein said oscillating sequence is comprised of:

$$\frac{\pi}{2} - T_m - T'_{cp} - [\pi - 2T_{cp}]_N$$

where $$T_{cp}' = T_{cp} - \frac{2t_{\frac{\pi}{2}}}{\pi},$$

$T_{cp}$ is a waiting period, $T_m$ is a waiting period where $|T_m|<T'_{cp}$, and $t_{\pi/2}$ is the duration of the $\pi/2$ pulse.

19. The method of claim 15, wherein said sequence produces more than one echo.

20. The method of claim 15, further comprising repeating (b) and (c) one or more times.

21. The method of claim 15, wherein said sequence of oscillating magnetic field pulses is comprised of:

$$\pi/2-\delta-\pi/2-T_d-\pi/2-T_{cp}-[\pi-2T_{cp}]_n$$

where $T_d$ is the initial diffusion time, $T_{cp}$ is a waiting period.

22. The method of claim 15, further comprising applying a CPMG sequence to said fluid and detecting magnetic resonance signals.

23. The method of claim 15, wherein said sequence of oscillating magnetic field pulses is comprised of:

$$\pi/2-\delta/2-\theta_1\delta/2-\theta_2-T_{cp}-[\pi-2T_{cp}]_n$$

where $T_{cp}$ is a waiting period.

24. A logging apparatus comprising:
 a logging tool that is moveable through a formation containing a fluid; and
 a processor that is coupled with the logging tool, the processor being programmed with instructions which, when executed by the processor:
  cause the logging tool to:
   i) generate a sequence of oscillating magnetic field pulses to said fluid wherein said sequence includes a first portion followed by a second portion, wherein said first portion spatially modulates the magnetization state of the fluid and said second portion monitors the evolution of said modulation, wherein said sequence is generated in the presence of a strong magnetic field gradient;
   ii) detect magnetic resonance signals produced from said fluid;
  and cause the processor to:
   v) analyze the detected magnetic resonance signals to determine any molecular displacement of said fluid.

25. The apparatus of claim 24, wherein said strong magnetic field gradient is greater than $1/\gamma Lt_\pi$, where $\gamma$ is the gyromagnetic ratio of the nuclei of said fluid, L is the sample length along the gradient direction, and $t_\pi$ is the duration of the $\pi$ pulse.

26. The apparatus of claim 24 wherein the processor analyzes the detected signals to determine the diffusion of the fluid.

27. The apparatus of claim 24 wherein the processor analyzes the detected signals to determine the restricted diffusion of the fluid.

28. The apparatus of claim 24 wherein the processor analyzes the detected signals to determine the velocity of the fluid.

29. The apparatus of claim 24 wherein the processor analyzes the detected signals to determine the acceleration of the fluid.

30. The apparatus of claim 24, wherein said oscillating sequence is comprised of:

$$\frac{\pi}{2} - T_m - T'_{cp} - [\pi - 2T_{cp}]_N$$

where $$T_{cp}' = T_{cp} - \frac{2t_{\frac{\pi}{2}}}{\pi},$$

$T_{cp}$ is a waiting period, $T_m$ is a waiting period where $|T_m|<T'_{cp}$, and $t_{\pi/2}$ is the duration of the $\pi/2$ pulse.

31. The apparatus of claim 24, wherein said sequence produces more than one echo.

32. The apparatus of claim 24, wherein said sequence of oscillating magnetic field pulses is comprised of:

$$\pi/2-\delta-\pi/2-T_d-\pi/2-T_{cp}-[\pi-2T_{cp}]_n$$

where $T_d$ is a the initial diffusion time, $T_{cp}$ is a waiting period.

33. The apparatus of claim 24, wherein the said instructions further cause the processor to apply a CPMG sequence to said fluid and detecting magnetic resonance signals.

34. The apparatus of claim 24, wherein said sequence of oscillating magnetic field pulses is comprised of:

$$\pi/2-\delta/2-\theta_1-\delta/2-\theta_2 T_{cp}-[\pi-2T_{cp}]_n$$

where $T_{cp}$ is a waiting period.

35. A method of measuring magnetization transfer by chemical exchange of a sample comprising:

a) applying a sequence of oscillating magnetic field pulses to said sample wherein said sequence includes a first portion followed by a second portion, wherein said first portion induces a chemical shift modulation of said sample and said second portion monitors the evolution of said modulation;

b) detecting magnetic resonance signals from said sample; and c) analyzing said detected signals to determine the magnetization transfer of said sample.

\* \* \* \* \*